US008685367B2

(12) United States Patent
Brandom et al.

(10) Patent No.: US 8,685,367 B2
(45) Date of Patent: Apr. 1, 2014

(54) INHERENTLY RADIOPAQUE POLYMERIC PRODUCTS FOR EMBOLOTHERAPY

(75) Inventors: Donald K. Brandom, San Diego, CA (US); Eric Schmid, San Diego, CA (US); Joan Zeltinger, Encinitas, CA (US); Durgadas Bolikal, Edison, NJ (US); Joachim B. Kohn, Plainfield, NJ (US)

(73) Assignee: Rutgers, The State University of of New Jersey, New Brunswick, NJ (US)

( * ) Notice: Subject to any disclaimer, the term of this patent is extended or adjusted under 35 U.S.C. 154(b) by 1004 days.

(21) Appl. No.: 10/952,274

(22) Filed: Sep. 27, 2004

(65) Prior Publication Data
US 2005/0106119 A1 May 19, 2005

Related U.S. Application Data

(60) Provisional application No. 60/601,677, filed on Aug. 13, 2004, provisional application No. 60/505,951, filed on Sep. 25, 2003.

(51) Int. Cl.
*A61K 51/00* (2006.01)
*A61M 36/14* (2006.01)

(52) U.S. Cl.
USPC ....... 424/1.29; 424/1.11; 424/1.33; 424/1.65; 424/9.1

(58) Field of Classification Search
USPC ............. 424/1.11, 1.65, 1.81, 1.85, 1.89, 9.1, 424/9.6; 428/412, 474.4, 480; 525/408, 525/409, 430, 437, 439, 447, 449, 534, 540
See application file for complete search history.

(56) References Cited

U.S. PATENT DOCUMENTS

| | | | |
|---|---|---|---|
| 4,441,495 A | 4/1984 | Hicswa | 606/195 |
| 4,819,637 A | 4/1989 | Dormandy, Jr. et al. | 606/195 |
| 4,980,449 A * | 12/1990 | Kohn et al. | 528/211 |
| 5,099,060 A * | 3/1992 | Kohn et al. | 560/40 |
| 5,216,115 A | 6/1993 | Kohn et al. | 528/176 |
| 5,219,564 A | 6/1993 | Zalipsky et al. | 424/78.17 |
| 5,317,077 A | 5/1994 | Kohn et al. | 528/182 |
| 5,587,507 A | 12/1996 | Kohn et al. | 560/40 |
| 5,658,995 A | 8/1997 | Kohn et al. | 525/432 |
| 5,660,822 A | 8/1997 | Poiani et al. | 424/78.17 |
| 5,670,602 A | 9/1997 | Kohn et al. | 528/176 |
| 5,733,328 A | 3/1998 | Fordenbacher | 623/1.16 |
| 5,851,508 A | 12/1998 | Greff et al. | 424/9.411 |
| 5,877,224 A | 3/1999 | Brocchini et al. | 514/772.2 |
| 6,015,541 A * | 1/2000 | Greff et al. | 424/1.25 |
| 6,048,521 A | 4/2000 | Kohn et al. | 424/78.08 |
| 6,103,255 A | 8/2000 | Levene et al. | 424/426 |
| 6,117,157 A | 9/2000 | Tekulve | 606/200 |
| 6,120,491 A | 9/2000 | Kohn et al. | 604/502 |
| RE37,160 E | 5/2001 | Kohn et al. | 560/40 |
| 6,284,862 B1 | 9/2001 | Kohn et al. | 528/176 |
| 6,319,492 B1 | 11/2001 | Kohn et al. | 424/78.08 |
| 6,337,198 B1 | 1/2002 | Levene et al. | 435/174 |
| 6,342,202 B1 * | 1/2002 | Evans et al. | 424/9.42 |
| 6,358,228 B1 | 3/2002 | Tubman et al. | 604/104 |
| 6,475,477 B1 | 11/2002 | Kohn et al. | 424/78.08 |
| 6,531,111 B1 * | 3/2003 | Whalen et al. | 424/9.45 |
| 7,250,154 B2 * | 7/2007 | Kohn et al. | 424/9.6 |
| 2006/0024266 A1 | 2/2006 | Brandom et al. | |
| 2006/0036316 A1 | 2/2006 | Zeltinger et al. | |
| 2006/0182779 A1 | 8/2006 | Brandom et al. | |

FOREIGN PATENT DOCUMENTS

| | | |
|---|---|---|
| JP | 2003528130 T | 9/2003 |
| WO | 93/10824 A1 | 6/1993 |
| WO | 96/30331 A1 | 10/1996 |
| WO | WO97/04744 | 2/1997 |
| WO | 98/46286 A1 | 10/1998 |
| WO | WO 9846286 A1 * | 10/1998 |
| WO | 99/24391 A1 | 5/1999 |
| WO | 0172281 A2 | 10/2001 |
| WO | 01/85214 A1 | 11/2001 |
| WO | 03007785 A2 | 1/2003 |

OTHER PUBLICATIONS

S. Murthy Tadavarthy et al., "Polyvinyl Alcohol (Ivalon)—a New Embolic Material," american Journal of Roentgenology: Radium Therapy and Nuclear Medicine, vol. 125, pp. 609-616, (1975).
William O. Bank, *Gelfoam Embolization: A Simplified Technique*, 132 AJR 299-301 (Feb. 1979).
John D. Barr et al., *Polyvinyl Alcohol Foam Particle Sizes and Concentrations Injectable Through Microcatheters*, 9 JVIR 113-18 (1998).
Israel Cabasso et al., *Radiopaque Miscible Systems Composed of Poly(Methyl Methacrylate) and Transition and Nontransition Metal Salts: Spectroscopic, Thermal, and Radiographic Chacterization*, 38 Journal of Applied Polymer Science 1653-66 (1989).
Israel Cabasso et al., *Radiopaque Polymers Based on Acrylated Phosphonate Esters Derived from Polyols*, 41 Journal of Applied Polymer Science 3025-42 (1990).
Colin P. Derdeyn et al., *Polyvinyl Alcohol Particle Size and Suspension Characteristics*, 16 Am. J. Neuroradiol. 1335-43 (Jun. 1995).
Sadek K. Hilal et al., *Therapeutic Percutaneous Embolization for Extra-Axial Vascular Lesions of the Head, Neck, and Spine*, 43 J. Neurosurg. 275-87 (Sep. 1975).
Daniel Horak et al., *Hydrogels in Endovascular Embolization. III. Radiopaque Spherical Particles, Their Preparation and Properties*, 8 Biomaterials 142-45 (Mar. 1987).
Daniel Horak et al., *Hydrogels in Endovascular Embolization IV. Effect of Radiopaque Spherical Particles on the Living Tissue*, 9 Biomaterials 367-71 (Jul. 1988).
A. Jayakrishnan and B.C. Thanoo, *Synthesis and Polymerization of Some Iodine-Containing Monomers for Biomedical Applications*, 44 Journal of Applied Polymer Science 743-48 (1992).
Charles W. Kerber, *Catheter Therapy: Fluoroscopic Monitoring of Deliberate Embolic Occlusion*, 125 Radiology 538-40 (Nov. 1977).
Charles W. Kerber, *Polyvinyl Alcohol Foam: Prepackaged Emboli for Therapeutic Embolization*, 130 Am. J. Roentgenol 1193-94 (Jun. 1978).
Charles W. Kerber, *Flow-Controlled Therapeutic Embolization: A Physiologic and Safe Technique*, 1 AJNR 77-81 (1980).
Marc-Anton B. Kruft et al., *Studies on Radio-opaque Polymeric Biomaterials With Potential Applications to Endovascular Prostheses*, 17 Biomaterials 1803-12 (1996).

(Continued)

Primary Examiner — D L Jones
(74) *Attorney, Agent, or Firm* — Fox Rothschild LLP

(57) ABSTRACT

Preferred embodiments relate to compositions of inherently radiopaque, biocompatible, bioresorbable polymeric particles and methods of using them for embolizing a body lumen.

13 Claims, 3 Drawing Sheets

(56) References Cited

OTHER PUBLICATIONS

Marc-Anton B. Kruft et al., *In vivo Tissue Compatibility of Two Radio-opaque Polymeric Biomaterials*, 18 Biomaterials 31-6 (1997).

J.K. Latta and K. Sapna, *Biodegradable Microspheres of Poly(DL-lactic acid) Containing Piroxicam As a Model Drug for Controlled Release Via the Parenteral Route*, 10(4) J. Microencapsulation 449 (1993).

Richard E. Latchaw and Lawrence H.A. Gold, *Polyvinyl Foam Embolization of Vascular and Neoplastic Lesions of the Head, Neck, and Spine*, 131 Radiology 669-79 (Jun. 1979).

Daniel P. Link et al., *Hydrogel Embolic Agents: Theory and Practice of Adding Radio-opacity*, 29 Investigative Radiology 746-51 (Aug. 1994).

H.Q. Mao et al., *Synthesis and Biological Properties of Polymer Immunoadjuvants*, 25(5) Polymer Journal 499-505 (1993).

Sylvain Moreau et al., *Supraselective Embolization in Intractable Epistaxis: Review of 45 Cases*, 108 Laryngoscope 887-88 (Jun. 1998).

Norbert Moszner et al., *Synthesis and Polymerization of Hydrophobic Iodine-Containing Methacrylates*, 224 Die Angewandte Makromoleculare Chemie 115-23 (1995).

Aruna Nathan et al., *Hydrogels Based on Water-Soluble Poly(ether urethanes) Derived from L-Lysine and Poly(ethylene glycol)*, 25 Macromolecules 4476-84 (1992).

Aruna Nathan et al., *Copolymers of Lysine and Polyethylene Glycol: A New Family of Functionalized Drug Carriers*, 4 Bioconjugate Chemistry 54-62 (1993).

D. Novak, *Embolization Materials, in* Interventional Radiology 295-313 (Dandlinger et al., eds. 1990).

J.H. Ravina et al., *Arterial Embolisation to Treat Uterine Myomata*, 346 Lancet 671-72 (Sep. 1995).

Brian Solomon et al., *Chemoembolization of Hepatocellular Carcinoma with Cisplatin, Doxorubicin, Mitomycin-C, Ethiodol, and Polyvinyl Alcohol: Prospective Evaluation of Response and Survival in a U.S. Population*, 10 JVIR 793-98 (Jun. 1999).

Ewen Y. Tseng et al., *Angiographic Embolization for Epistaxis: A Review of 114 Cases*, 108 Laryngoscope 615-19 (Apr. 1998).

Benzina et al., A versatile three-iodine molecular building block leading to new radiopaque polymeric biomaterials, Journal of Biomedical Materials Research, Nov. 1, 1996, pp. 459-466, vol. 32, John Wiley & Sons, Inc., US.

Horak, et al. "New radiopaque polyHEMA-based hydrogel particles". Journal of Biomedical Materials Research 34: 183-188. (1997).

\* cited by examiner

INHERENTLY RADIOPAQUE POLYMERIC PRODUCTS FOR EMBOLOTHERAPY

RELATED APPLICATIONS

This application claims priority under 35 U.S.C. §119(e) to U.S. Provisional Application No. 60/601,677 filed Aug. 13, 2004 and U.S. Provisional Application No. 60/505,951 filed Sep. 25, 2003. The disclosures of both applications are incorporated herein by reference.

FIELD OF INVENTION

Preferred embodiments of the present invention relate to inherently radiopaque, biocompatible, bioresorbable polymeric particles and methods of using them for embolizing a body lumen.

BACKGROUND

Embolotherapy devices and reagents include metal embolic coils, gel foams, glues, oils, alcohol or particulate polymeric embolic agents used, for example, to control bleeding, prevent blood loss prior to or during a surgical procedure, restrict or block blood supply to tumors and vascular malformations, e.g., for uterine fibroids, tumors (i.e., chemo-embolization), hemorrhage (e.g., during trauma with bleeding) and arteriovenous malformations, fistulas and aneurysms. Embolic coils and particles are the most commonly used.

Conventional embolic coils are generally coiled metal strands that are constrained to a linear configuration during delivery through a vascular catheter. They have a geometrically preformed 'coiled' state to which they recover upon exiting the delivery catheter. There are a number of different design and procedural variations used with metal coils (see e.g., U.S. Pat. Nos. 6,358,228 and 6,117,157); however, metal embolic coils are designed to exploit the first response, i.e., a blood clot due to the hemodynamic response of a physical obstruction in the blood flow and in some cases an additional response i.e., a blood clot due to the biological response of the body to the coil material, wherein the therapeutic goal of the blocking the blood flow is accomplished by clot formation within and around the metal coil.

Although metal embolic coils have some advantageous physicomechanical properties, such as inherent radiopacity and shape memory (i.e., return to the preformed coiled state upon deployment), there are a number of disadvantages associated with the use of metal embolic coils, including inter alia, chronic tissue damage, tissue hyperplasia, vessel occlusion and permanent incorporation into the tissue at the deployment site.

Non-metallic alternatives include liquid and particulate embolic agents. However, these also have significant disadvantages. Liquid embolic agents are generally divided into precipitative and reactive systems. In the former case, a polymer is solvated within a biologically acceptable solvent that dissipates upon vascular delivery leaving the polymer to precipitate in situ (see e.g., U.S. Pat. No. 5,851,508). Such agents may not precipitate quickly enough, thereby allowing a non-solidified (viscous) polymer embolic to migrate and embolize unintended tissues. This is of particular concern with arteriovenous malformations wherein the material can easily enter the venous system and cause a significant pulmonary embolism. Another disadvantage is the use of solvents, such asdimethylsulfoxide, for delivering the precipitative polymers.

Reactive embolic agents are primarily variations of cyanoacrylate chemical systems. An example of an FDA approved system is the TRUFILL® cyanoacrylate embolic from Cordis. Here, a liquid monomeric and/or oligomeric cyanoacrylate mixture is introduced to the vascular site through a catheter wherein polymerization is initiated by the available water in the blood. Unfortunately, if the dwell time during delivery is too great, the cyanoacrylate adhesive may bond the catheter tip to the tissues with grave consequences. A secondary concern is that the bioresorbable degradation products from these materials include formaldehyde, a toxic chemical.

Particulate therapeutic emboli are composed of particles of various size, geometry and composition. Schwarz et al., *J. Biomater.*, 25(21), 5209-15 (2004) disclosed degradable hydroxy-ethyl acrylate (HEA) microspheres have been synthesized and tested in animals but none have been commercialized. The particles used for clinical applications are typically suspended in a radiopaque contrast solution and delivered through a vascular catheter via syringe injection. The three most common particulate embolic agents currently being used are GELFOAM® (absorbable gelatin particles from Pharmacia & Upjohn), polyvinyl alcohol (PVA) foam and trisacryl gelatin microspheres (EMBOSPHERE® from Biosphere Medical). Unlike metallic coils, these embolics are not inherently radiopaque. Indeed, placement visualization is dependent upon inference from fluoroscopic flow analysis during the embolic procedure. There is no direct ability to visualize the actual particles once inside the body. Also, in the case of PVA and EMBOSPHERE, the material may reside in the body throughout the patient's lifetime providing an increased risk of biological rejection. In the case of GEL-FOAM, there is the possibility of tissue rejection of this animal derived agent.

Particulate embolic agents may be used, for example, to restrict or block blood supply as in traditional applications which generally include delivery through a guide catheter such as treatment of tumors and vascular malformations, e.g., for uterine fibroids, cancerous tumors (i.e., chemo-embolization), hemorrhage (e.g., during trauma with bleeding) and arteriovenous malformations, fistulas and aneurysms.

Biocompatible, bioresorbable particulate embolic agents have the potential advantage of being temporary. The effective removal of the particulate foreign body over time allows the tissue to return to its unaffected state.

Radiopaque embolic particulate agents have the potential distinct advantage of being visible during and after embolic therapy procedures. During the procedure, visualization of the particulate agent would allow the physician to affect precise delivery to the targeted vessel or tissue. That is, the physician would be able to ensure that the particles do not become resident in unintended sites. This level of control would greatly enhance the safety and effectiveness of embolotherapy. Once the radiopaque particles have been implanted, follow-up procedures could be limited to non-interventional methods, e.g., simple X-Ray radiography. In the case of a tumor, for example, its size could be tracked since the radiopaque embolized sections would be shown converge as the mass/volume decreased with time.

As noted, biocompatible embolic particles exist on the market today. Indeed, bioresorbable biocompatible embolic agents are available in the form of GELFOAM®. As noted, however, there is a potential for rejection due to the animal origin of this material. Furthermore, GELFOAM® is not an FDA approved device for this application.

Attempts have been made to produce a more biocompatible degradable embolic particulate agent. Likewise, investigational radiopaque embolic agents have been produced and tested in animals for their potential utility. In all cases external agents such as iodinated contrast media or a metal or its salt (e.g., tungsten, barium sulfate, etc) must be added or inherent radiopacity imparted by halogenation of non-bioresorbable compositions.

Heretofore however, biocompatible, bioresorbable, inherently radiopaque particles for embolotherapy have not been conceived nor attempted. Accordingly, there remains an important unmet need to develop biocompatible, bioresorbable, inherently radiopaque particles for embolotherapy, which may also allow for repeat treatment of the same site, while circumventing or alleviating the foregoing disadvantages of existing or conceived particulate embolic agents.

Accordingly, there remains an important unmet need to develop bioresorbable, radiopaque embolic agents, wherein the polymeric materials used to fabricate these agents have the desirable qualities of metal (e.g., radiopacity), while circumventing or alleviating the foregoing disadvantages associated with the use of metal coils or liquid and particulate embolic alternatives.

SUMMARY OF THE INVENTION

An embolotherapy product is disclosed in accordance with preferred embodiments of the present invention. The embolotherapy product comprises a particulate formulation comprising a biocompatible, bioresorbable polymer, and optionally including the stereoisomers thereof, wherein the polymer comprises a sufficient number of halogen atoms to render the embolotherapy product inherently radiopaque. In some preferred embodiments, the polymer comprises a homopolymer, a heteropolymer, or a blend thereof.

In one preferred embodiment of the embolotherapy product, the polymer comprises one or more units described by Formula I:

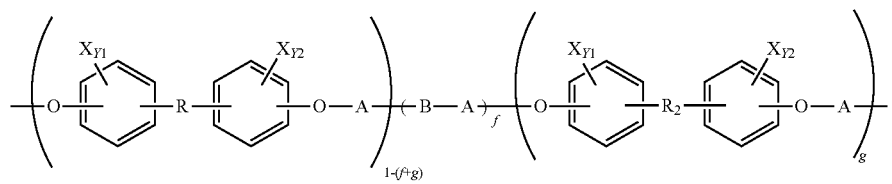

(I)

wherein X=I or Br; Y1 and Y2 can independently=0, 1, 2, 3 or 4;

wherein f is between 0 and less than 1; g is between 0 and 1, inclusive; and f+g is between 0 and 1, inclusive;

wherein A is either:

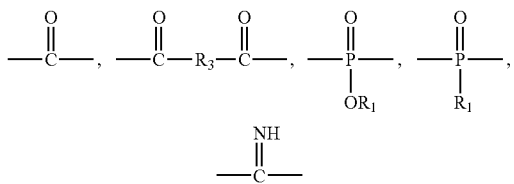

wherein $R_1$ is independently an H or an alkyl group ranging from 1 to about 18 carbon atoms containing from 0 to 5 heteroatoms selected from O and N;

wherein $R_3$ is a saturated or unsaturated, substituted or unsubstituted alkyl, aryl, or alkylaryl group containing up to about 18 carbon atoms and 0 to 8 heteroatoms selected from O and N;

wherein B is an aliphatic linear or branched diol or a poly(alkylene glycol) unit; and wherein R and $R_2$ may be independently selected from:

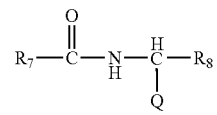

wherein $R_7$ is selected from the group consisting of —CH=CH—, —$CHJ_1$-$CHJ_2$- and (—$CH_2$—)a;

wherein $R_8$ is selected from the group consisting of —CH=CH—, —$CHJ_1$-$CHJ_2$- and (—$CH_2$—)n;

wherein a and n are independently between 0 and 8 inclusive; $J_1$ and $J_2$ are independently Br or I; and, for $R_2$, Q comprises a free carboxylic acid group, and, for R, Q is selected from the group consisting of hydrogen and carboxylic acid esters and amides, wherein said esters and amides are selected from the group consisting of esters and amides of alkyl and alkylaryl groups containing up to 18 carbon atoms and esters and amides of biologically and pharmaceutically active compounds.

In a variation to this embodiment of Formula I, R and $R_2$ may be selected from the groups:

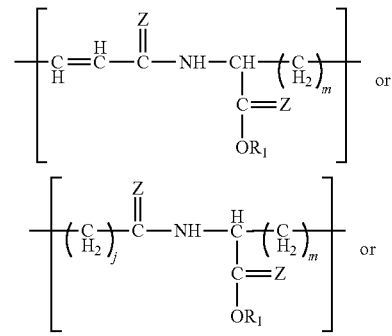

-continued

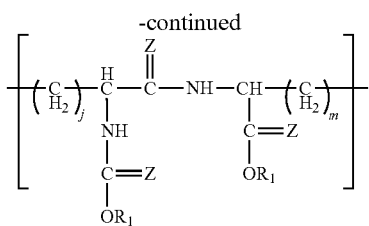

wherein $R_1$ in each $R_2$ is independently an alkyl group ranging from 1 to about 18 carbon atoms containing from 0 to 5 heteroatoms selected from O and N and $R_1$ in each R is H;

wherein j and m are independently integers from 1 to 8 inclusive; and wherein Z is independently either O or S.

In another preferred embodiment of the embolotherapy product, the polymer may comprise one or more units described by Formula II:

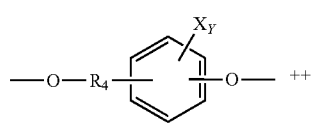

(II)

wherein X for each polymer unit is independently Br or I, Y is between 1 and 4, inclusive and $R_4$ is an alkyl, aryl or alkylaryl group with up to 18 carbon atoms and from 0 to 8 heteroatoms selected from O and N.

In variations to the polymer of Formula II, all X groups may be ortho-directed and Y may be 1 or 2. In another variation, $R_4$ is an alkyl group.

In another variation, $R_4$ has the structure:

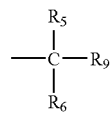

wherein $R_9$ for each unit is independently an alkyl, aryl or alkylaryl group containing up to 18 carbon atoms and from 0 to 8 heteroatoms selected from O and N; and $R_5$ and $R_6$ are each independently selected from hydrogen and alkyl groups having up to 18 carbon atoms and from 0 to 8 heteroatoms selected from O and N.

In another variation to $R_4$ in Formula II, $R_9$ for at least one unit comprises a pendant $COOR_1$ group, wherein, for each unit in which it is present, the subgroup $R_1$ is independently a hydrogen or an alkyl group ranging from 1 to about 18 carbon atoms containing from 0 to 5 heteroatoms selected from O and N.

In another variation to $R_4$ in Formula II, $R_9$ independently has the structure:

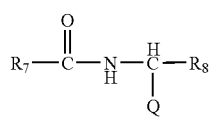

wherein $R_7$ is selected from the group consisting of —CH=CH—, —$CHJ_1$-$CHJ_2$- and (—$CH_2$—)a, wherein $R_8$ is selected from the group consisting of —CH=CH—, —$CHJ_1$-$CHJ_2$- and (—$CH_2$—)n, wherein a and n are independently between 0 and 8 inclusive; and $J_1$ and $J_2$ are independently Br or I; and Q is selected from the group consisting of hydrogen, a free carboxylic acid group, and carboxylic acid esters and amides, wherein said esters and amides are selected from the group consisting of esters and amides of alkyl and alkylaryl groups containing up to 18 carbon atoms and esters and amides of biologically and pharmaceutically active compounds.

In another variation to $R_4$ in Formula II, $R_9$ independently has the structure:

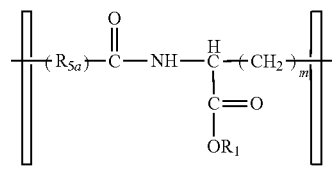

wherein $R_{5a}$ is an alkyl group containing up to 18 carbon atoms and from 0 to 5 heteroatoms selected from O and N; and wherein m is an integer from 1 to 8 inclusive; and $R_1$ is independently a hydrogen or an alkyl group ranging from 1 to about 18 carbon atoms containing from 0 to 5 heteroatoms selected from O and N.

In another variation to $R_4$ in Formula II, $R_9$ independently has the structure:

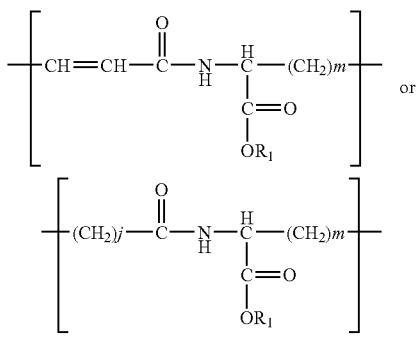

wherein j and m are independently an integer from 1 to 8, inclusive, and $R_1$ is independently a hydrogen or an alkyl group ranging from 1 to about 18 carbon atoms containing from 0 to 5 heteroatoms selected from O and N.

In some embodiments of the embolotherapy products of the present invention, the polymer may be copolymerized with a poly($C_1$-$C_4$ alkylene glycol). Preferably, the poly($C_1$-$C_4$ alkylene glycol) is present in a weight fraction of less than about 75 wt %. More preferably, the poly(alkylene glycol) is poly(ethylene glycol).

In another variation to the polymers disclosed herein, between about 0.01 and about 0.99 percent of said polymer units comprise a pendant —COOH group.

In another variation to Formula II, $R_4$ may be an aryl or alkylaryl group. Preferably, the $R_4$ aryl or alkylaryl group is selected so that the polymer units are diphenols.

In another preferred embodiment of the embolotherapy product, the polymer may comprise one or more units described by Formula III:

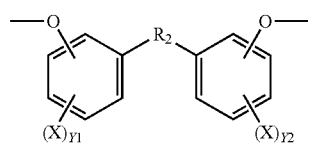

(III)

wherein X for each polymer unit is independently Br or I, Y1 and Y2 are each independently between 0 and 4, inclusive, Y1+Y2 for each unit is independently between 1 and 8, inclusive, and $R_2$ for each polymer unit is independently an alkyl, aryl or alkylaryl group containing up to 18 carbon atoms and from 0 to 8 heteroatoms selected from O and N.

In preferred variations to Formula III, all X groups are ortho-directed. Preferably, Y1 and Y2 are independently 2 or less, and Y1+Y2=1, 2, 3 or 4.

In another variation to Formula III, $R_2$ for at least one unit may comprise a pendant $COOR_1$ group, wherein, for each unit in which the $COOR_1$ group is present, the subgroup $R_1$ is independently a hydrogen or an alkyl group ranging from 1 to about 18 carbon atoms containing from 0 to 5 heteroatoms selected from O and N.

In another variation to Formula III, $R_2$ independently has the structure:

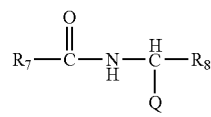

wherein $R_7$ is selected from the group consisting of —CH=CH—, —$CHJ_1$-$CHJ_2$- and (—$CH_2$—)a, wherein $R_8$ is selected from the group consisting of —CH=CH—, —$CHJ_1$-$CHJ_2$- and (—$CH_2$—)n, wherein a and n are independently between 0 and 8 inclusive; and $J_1$ and $J_2$ are independently Br or I; and Q is selected from the group consisting of hydrogen, a free carboxylic acid group, and carboxylic acid esters and amides, wherein said esters and amides are selected from the group consisting of esters and amides of alkyl and alkylaryl groups containing up to 18 carbon atoms and esters and amides of biologically and pharmaceutically active compounds.

In another variation to Formula III, $R_2$ independently has the structure:

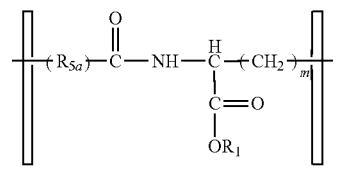

wherein $R_{5a}$ is an alkyl group containing up to 18 carbon atoms and from 0 to 5 heteroatoms selected from O and N; and wherein m is an integer from 1 to 8 inclusive; and $R_1$ is independently a hydrogen or an alkyl group ranging from 1 to about 18 carbon atoms containing from 0 to 5 heteroatoms selected from O and N.

In another variation to Formula III, $R_2$ independently has the structure:

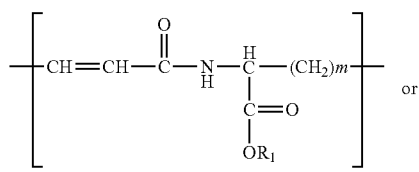

or

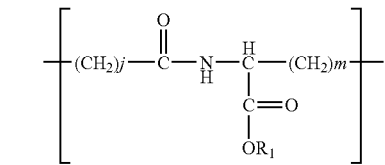

wherein j and m are independently an integer from 1 to 8, inclusive, and $R_1$ is independently a hydrogen or an alkyl group ranging from 1 to about 18 carbon atoms containing from 0 to 5 heteroatoms selected from O and N.

In a preferred variation to Formula III, between about 0.01 and about 0.99 percent of the polymer units comprise a pendant COOH group. Preferably, the polymer is copolymerized with up to 75 wt % of a poly($C_1$-$C_4$ alkylene glycol). More preferably, the poly($C_1$-$C_4$ alkylene glycol) is poly(ethylene glycol).

In another preferred embodiment of the embolotherapy product, the polymer may comprise one or more units described by Formula IV:

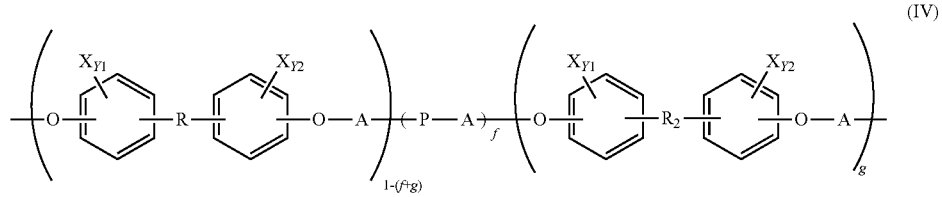

(IV)

wherein each X is independently I or Br, Y1 and Y2 for each diphenol unit are independently between 0 and 4, inclusive, and Y1+Y2 for each diphenol unit is between 1 and 8, inclusive;

each R and $R_2$ are independently an alkyl, aryl or alkylaryl group containing up to 18 carbon atoms and from 0 to 8 heteroatoms selected from O and N, wherein $R_2$ further comprises a pendant carboxylic acid group;

wherein A is either:

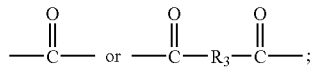

wherein $R_3$ is a saturated or unsaturated, substituted or unsubstituted alkyl, aryl, or alkylaryl group containing up to about 18 carbon atoms and 0 to 8 heteroatoms selected from O and N;

P is a poly($C_1$-$C_4$ alkylene glycol) unit having a weight fraction of about 75% or less; f is between 0 and less than 1, g is between 0 and 1, inclusive; and f+g is between 0 and 1, inclusive.

In preferred variations to Formula IV, P is a poly(ethylene glycol) that is present in a weight fraction of about 50% or less. More preferably, P is a poly(ethylene glycol) that is present in a weight fraction of about 30% or less.

In other preferred variations to Formula IV, both R and $R_2$ comprise a pendant $COOR_1$ group; wherein for R, the subgroup $R_1$ is independently an alkyl group ranging from 1 to about 18 carbon atoms containing from 0 to 5 heteroatoms selected from O and N; and wherein for $R_2$, the subgroup $R_1$ is a hydrogen atom.

In other preferred variations to Formula IV, each R and $R_2$ independently has the structure:

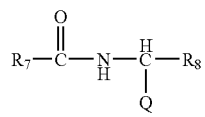

wherein $R_7$ is selected from the group consisting of —CH=CH—, —$CHJ_1$-$CHJ_2$- and (—$CH_2$—)a, wherein $R_8$ is selected from the group consisting of —CH=CH—, —$CHJ_1$-$CHJ_2$- and (—$CH_2$—)n, wherein a and n are independently between 0 and 8 inclusive; and $J_1$ and $J_2$ are independently Br or I; and Q for $R_2$ comprises a free carboxylic acid group, and Q for each R is independently selected from the group consisting of hydrogen, carboxylic acid esters and amides, wherein said esters and amides are selected from the group consisting of esters and amides of alkyl and alkylaryl groups containing up to 18 carbon atoms and esters and amides of biologically and pharmaceutically active compounds.

In other preferred variations to Formula IV, each $R_2$ independently has the structure:

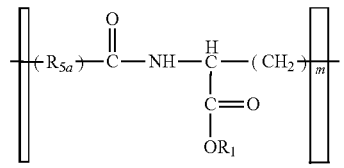

wherein $R_{5a}$ is an alkyl group containing up to 18 carbon atoms and from 0 to 5 heteroatoms selected from O and N; and wherein m is an integer from 1 to 8 inclusive; and $R_1$ is a hydrogen.

In other preferred variations to Formula IV, each $R_2$ independently has the structure:

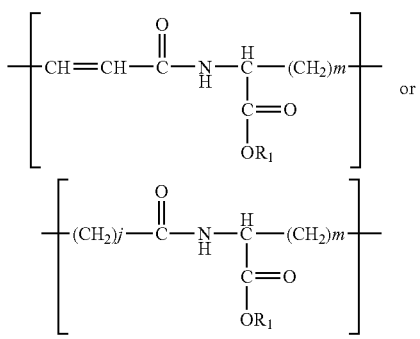

wherein j and m are independently an integer from 1 to 8, inclusive, and $R_1$ is a hydrogen. Preferably, each carboxylic acid ester or amide for R is either an ethyl or a butyl ester or amide.

In other preferred variations to Formula IV, A is a —C(=O)— group. In another preferred variation to Formula III, A is:

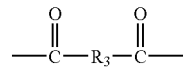

wherein $R_3$ is a $C_4$-$C_{12}$ alkyl, $C_8$-$C_{14}$ aryl, or $C_8$-$C_{14}$ alkylaryl. Preferably, $R_3$ is selected so that A is a moiety of a dicarboxylic acid that is a naturally occurring metabolite. More preferably, $R_3$ is a moiety selected from —$CH_2$—C(=O)—, —$CH_2$—$CH_2$—C(=O)—, —CH=CH— and (—$CH_2$—)$_z$, wherein z is an integer from 1 to 8, inclusive.

In other preferred variations to Formula IV, all X groups are ortho-directed. Preferbly, Y1 and Y2 are independently 2 or less, and Y1+Y2=1, 2, 3 or 4.

In other preferred variations to Formula IV, every halogen is iodine.

In other preferred variations to Formula IV, f is greater than 0.1 to about 0.3. Preferably, f is greater than 0.2 to about 0.25.

In other preferred variations to Formula IV, the poly($C_1$-$C_4$ alkylene glycol) weight fraction is less than about 25 wt %.

In other preferred variations to Formula IV, g is greater than 0.1 to about 0.35. More preferably, g is greater than 0.2 to about 0.3.

In another preferred embodiment of the embolotherapy product, the polymer may comprise one or more units described by Formula V:

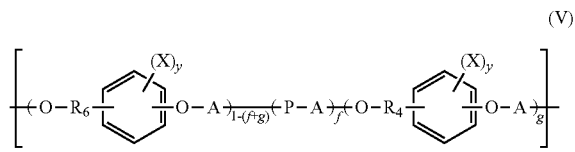

(V)

wherein each X is independently iodine or bromine; each y is independently between 0 and 4, inclusive, wherein a total number of ring-substituted iodine and bromine is between 1 and 8, inclusive; each $R_4$ and $R_6$ are independently an alkyl, aryl or alkylaryl group containing up to 18 carbon atoms and from 0 to 8 heteroatoms selected from O and N, and $R_4$ further includes a pendant carboxylic acid group;

wherein A is either:

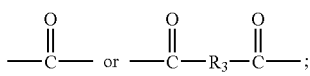

wherein $R_3$ is a saturated or unsaturated, substituted or unsubstituted alkyl, aryl, or alkylaryl group containing up to about 18 carbon atoms and 0 to 5 heteroatoms selected from the group consisting of O and N;

P is a poly($C_1$-$C_4$ alkylene glycol) unit present in a weight fraction of less than about 75 wt %;

f is from greater than 0 to less than 1; g is between 0 and 1, inclusive; and f+g is between 0 and 1, inclusive.

Preferably, P is a poly(ethylene glycol) unit.

In preferred variations to Formula V, each $R_4$ and $R_6$ of said polymer contains a pendant —$COOR_1$ group, wherein for each $R_6$, each subgroup $R_1$ is independently an alkyl group ranging from 1 to about 18 carbon atoms containing from 0 to 5 heteroatoms selected from the group consisting of O and N, and, for each $R_4$, each subgroup $R_1$ is a hydrogen atom.

In other preferred variations to Formula V, each $R_4$ and $R_6$ of said polymer are:

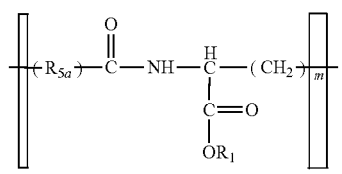

wherein $R_{5a}$ is an alkyl group containing up to 18 carbon atoms and from 0 to 5 heteroatoms selected from O and N; and wherein m is an integer from 1 to 8 inclusive; and for each $R_6$, each subgroup $R_1$ is independently an alkyl group ranging from 1 to about 18 carbon atoms containing from 0 to 5 heteroatoms selected from O and N, and, for each $R_4$, each subgroup $R_1$ is a hydrogen atom.

In other preferred variations to Formula V, each $R_1$ subgroup for $R_6$ of said polymer is either ethyl or butyl.

In other preferred variations to Formula V, A is a —C(=O)— group. Alternatively, A may be:

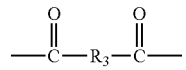

wherein $R_3$ is $C_4$-$C_{12}$ alkyl, $C_8$-$C_{14}$ aryl, or $C_8$-$C_{14}$ alkylaryl.

In other preferred variations to Formula V, $R_3$ is selected so that A is a moiety of a dicarboxylic acid that is a naturally occurring metabolite.

In other preferred variations to Formula V, $R_3$ is a moiety selected from the group consisting of —$CH_2$—C(=O)—, —$CH_2$—$CH_2$—C(=O)—, —CH=CH— and (—$CH_2$—)z, wherein z is an integer from 1 to 8, inclusive.

In other preferred variations to Formula V, all X groups are ortho-directed and y is 2 or 3.

In other preferred variations to Formula V, every X group is iodine.

In other preferred variations to Formula V, f is greater than 0.1 to about 0.3.

In other preferred variations to Formula V, g is greater than 0.1 to about 0.35.

In preferred embodiments of the embolotherapy product of the present invention, the particulate formulation may be configured for administration via injection. The formulation may comprises polymer particles selected from the group consisting of spherical particles, geometrically non-uniform particles, porous particles, hollow particles, solid particles, and particles having an excluded diameter of from about 10 microns to about 5,000 microns, and combinations thereof.

Alternatively, the formulation may comprise a polymer hydrogel composition.

In a preferred embodiment of the embolotherapy product, the polymer may further comprise an effective amount of at least one therapeutic agent. Preferably, the at least one therapeutic agent is selected from the group consisting of a chemotherapeutic agent, a non-steroidal anti-inflammatory, or a steroidal anti-inflammatory.

In another preferred embodiment of the embolotherapy product, the polymer may further comprise an effective amount of a magnetic resonance enhancing agent.

In a preferred embodiment of the embolotherapy product, the polymer may further comprise an effective amount of a radiopacifying agent, selected from the group consisting of iodine, bromine, barium, bismuth, gold, platinum, tantalum, tungsten, and mixtures thereof.

In another preferred embodiment of the embolotherapy product, the polymer may further comprise a biocompatible, bioresorbable polymeric coating adapted to promote a selected biological response. Preferably, the biological response is selected from the group consisting of thrombosis, cell attachment, cell proliferation, attraction of inflammatory cells, and deposition of matrix proteins, inhibition of thrombosis, inhibition of cell attachment, inhibition of cell proliferation, inhibition of inflammatory cells, and inhibition of deposition of matrix proteins or a combination thereof.

In another preferred embodiment of the embolotherapy product, the polymer may comprise Formula I:

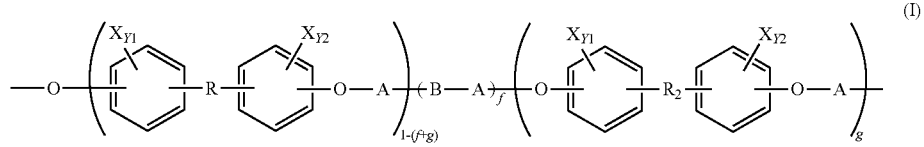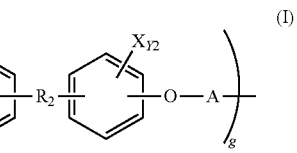

(I)

wherein X=I or Br; Y1 and Y2 can independently=0, 1, 2, 3 or 4;
wherein f is between 0 and less than 1; g is between 0 and 1, inclusive; and f+g is between 0 and 1, inclusive;
wherein R and $R_2$ may be independently selected from:

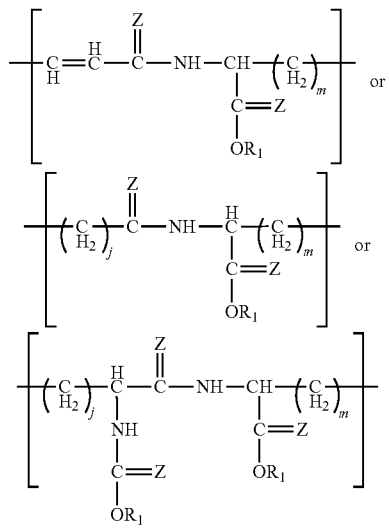

wherein, for $R_2$, $R_1$ is H and for R, $R_1$ is a long chain aliphatic hydrocarbon;
wherein j and m are independently integers from 1 to 8 inclusive;
wherein Z is independently either O or S;
wherein A is selected from the group consisting of:

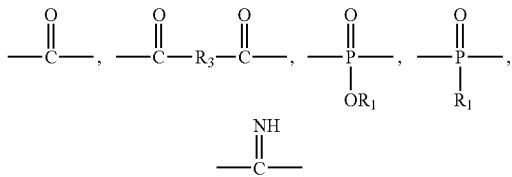

wherein $R_3$ is a saturated or unsaturated, substituted or unsubstituted alkyl, aryl, or alkylaryl group containing up to about 18 carbon atoms and 0 to 8 heteroatoms selected from O and N; and
wherein B is an aliphatic linear or branched diol, or a poly(alkylene glycol) unit.

A method for embolizing a body lumen is disclosed in accordance with another preferred embodiment of the present invention. The method comprises the step of introducing into the body lumen an effective amount of an embolotherapy product comprising a particulate formulation comprising a biocompatible, bioresorbable polymer, wherein the polymer comprises a sufficient number of halogen atoms to render the embolotherapy product inherently radiopaque.

Preferably, the step of introducing is accomplished by injection via either a catheter or syringe.

In another preferred embodiment of the present invention, a method of treating varicose and/or spider veins is disclosed. The method comprises administering within said varicose and/or spider veins an effective amount of an embolotherapy product comprising a particulate formulation comprising a biocompatible, bioresorbable polymer, wherein the polymer comprises a sufficient number of halogen atoms to render the embolotherapy product inherently radiopaque.

Preferably, the step of administering is accomplished by injection via either a catheter or syringe.

A method for enhancing the local delivery of a therapeutic agent to a tissue is also disclosed in accordance with preferred embodiments of the present invention. The method comprises the steps of: administering to a blood vessel associated with the tissue an amount of an embolotherapy product sufficient to reduce the blood flow from said tissue; administering the therapeutic agent to the blood vessel separately or in combination with the embolotherapy product, such that the local delivery of the therapeutic agent is enhanced; and repeating the steps of administering the embolotherapy product and therapeutic agent after the embolotherapy product first administered has degraded sufficiently to allow for re-access to said blood vessel. The embolotherapy product for use in this method comprises a particulate formulation comprising a biocompatible, bioresorbable polymer, wherein the polymer comprises a sufficient number of halogen atoms to render the embolotherapy product inherently radiopaque.

A method for re-treatment of a body lumen is also disclosed. The method comprises the steps of: administering to a region of a blood vessel associated with said tissue an amount of a biocompatible, bioresorbable polymeric embolotherapy product sufficient to reduce the blood flow from the tissue for a period of time; and administering at a later time any embolotherapy product, to the same approximate region of the blood vessel associated with said tissue such that the said tissue may be re-treated or allow for other forms of re-intervention.

In one embodiment of the embolotherapy product of the present invention, the polymer comprises a bioresorbable inherently radiopaque polymer that is not naturally occurring. In another variation, the polymer comprises a bioresorbable inherently radiopaque polymer comprising at least one amino acid.

BEST MODES OF CARRYING OUT THE INVENTION

Figure 1:
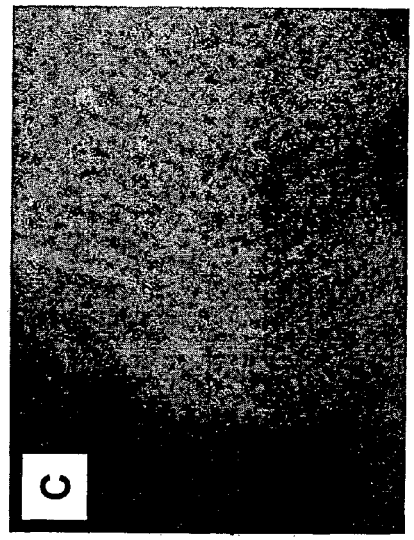
FIGS. 1A-1C depict x-ray views of an explanted porcine kidney injected with a radiopaque polymeric embolotherapy composition according to preferred embodiments.
Figure 1:
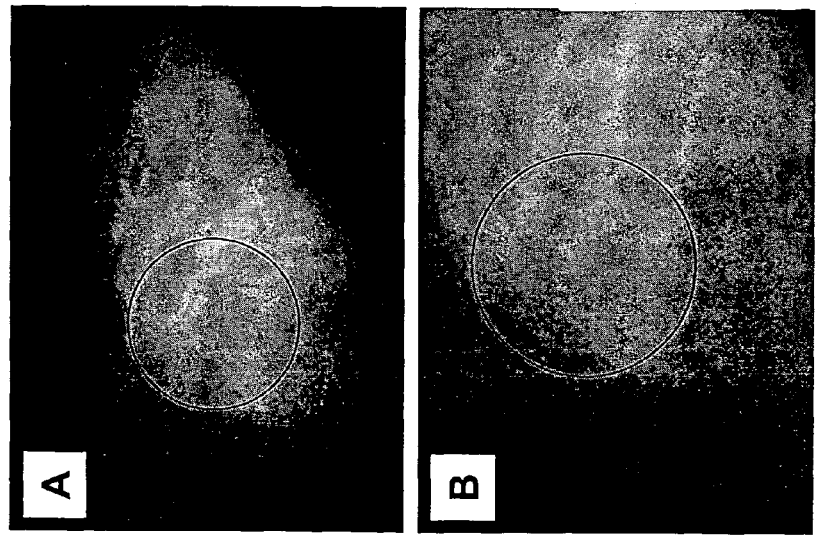

Bioresorbable, inherently radiopaque polymeric embolotherapy products are disclosed in accordance with preferred embodiments of the present invention. They may be used, for example, to temporarily restrict or block blood supply as in traditional applications which generally include delivery through a catheter such as treatment of tumors and vascular malformations, e.g., for uterine fibroids, tumors (i.e., chemoembolization), hemorrhage (e.g., during trauma with bleeding) and arteriovenous malformations, fistulas and aneurysms. Further these embolic agents may be delivered by other means, for example, directly into the body through a syringe or other non-catheter vehicle to provide cosmetic treatment for spider veins (unattractive or undesirable small, veins close to the skin surface that are tree branch-shaped or spider web-shaped and red or blue in color) found on both the legs and the face or even varicose veins (swollen and raised above the surface of the skin).

Embolotherapy products according to preferred aspects of the present invention can have at least some of the following attributes: (a) sufficient radiopacity to be visible by conventional X-ray fluoroscopy, (b) sufficient particle compressibility, flow and buoyancy attributes to fabricate embolotherapy delivery and functionality; (c) desirable surface properties or functionalities that can be adjusted to account for the needs (e.g., blood compatibility or thrombosis) for a range of applications; (d) desirable biodegradation and bioresorption profiles that can be adjusted to account for the needs of a range of applications involving blockage of a body lumen for different lengths of time; (e) desirable residence time in the body lumen with said tissue such that at a later time any embolic product may be used to re-treat the approximate same region of the blood vessel and said tissue or allow for other forms of re-treatment such as surgery; (f) an amount of a therapeutic sufficient to promote a desirable biological and/or physiological effect and/or (g) a biocompatible, bioresorbable coating sufficient to promote a desirable biological and/or physiological effect of an embolized body lumen. A body lumen is used herein to designate a vascular body lumen or blood vessel (i.e., arterial and/or venous vessel of any size) that comprises the body circulatory system.

According to one aspect of the present invention, an embolotherapy product is provided that is a particulate formulation of a biocompatible, bioresorbable polymer, wherein the polymer has a sufficient number of halogen atoms to render the embolotherapy product visible by conventional x-ray fluoroscopy.

Preferred embodiments of the present invention are directed to compositions and methods for embolizing or occluding a body lumen, preferably a blood vessel, by introducing therein a biocompatible, bioresorbable, particulate polymeric material. In more preferred embodiments the polymeric material incorporates a radiopaque moiety, preferably, a halogen, and most preferably an iodine and/or bromine. The term "bioresorbable" is used herein to designate polymers that undergo biodegradation (through the action of water and/or enzymes to be chemically degraded) and at least some of the degradation products are eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography).

Additionally, applicants have found that the halogenated polymers of the present invention exhibit a unique combination of properties that are particularly beneficial for embolotherapy use, including radiopacity, biocompatibility and bioabsorbability. These polymers may include for example, embodiments of the genus described in U.S. Pat. No. 6,475,477 (incorporated herein in its entirety by reference), and more particularly iodinated and/or brominated biocompatible diphenols and poly(alkylene glycols), which exhibit a unique combination of properties that are particularly beneficial for embolotherapy use. Significantly, while U.S. Pat. No. 6,475,477 describes a wide variety of polymers having various combinations of properties and characteristics, applicants have discovered presently that certain polymers exhibit a combination of properties that are significantly and surprisingly superior to those polymers disclosed in U.S. Pat. No. 6,475,477.

As used herein, an "embolotherapy product" means any polymeric formulation adapted to embolize a body lumen (e.g., control bleeding, prevent blood loss, and/or restrict or block blood flow). Examples include compositions such as injectable polymeric formulations, particles, hydrogels, and the like.

Embolotherapy products according to the preferred embodiments are prepared using conventional designs substituting the disclosed radiopaque, biocompatible, bioresorbable polymers for the non-therapeutic structural materials conventionally employed. Such products are inherently effective. The embolotherapy products according to the preferred embodiments are administered by conventional means in effective quantities to the site to be embolized.

Applicants have discovered that a biocompatible, bioresorbable, inherently radiopaque polymer class can be produced from a broad class of aryl-containing biocompatible, bioresorbable polymers. For example, in all of the biocompatible, bioresorbable polymers noted in the TABLE 1 below, radiopacity may be introduced to the aromatic rings via halogenation, particularly bromination and iodination, by well-known techniques that can be readily employed by those of ordinary skill in the art without undue experimentation. Indeed, U.S. Pat. No. 6,475,477 reveals a broad class of inherently radiopaque, biocompatible, bioresorbable polymers made in this manner. Radiopacity may be imparted to the monomeric components of the other polymers in this table in a like fashion.

TABLE 1

| U.S. Pat. | Patent Title | What is taught |
| --- | --- | --- |
| 6,475,477 | Radio-opaque polymer biomaterials | Iodine- and bromine-substituted diphenol monomer synthesis<br>Iodine- and bromine-substituted polycarbonate homopolymers and copolymer synthesis |

TABLE 1-continued

| U.S. Pat. | Patent Title | What is taught |
|---|---|---|
| | | Iodine- and bromine-substituted polyarylate homopolymers and copolymer synthesis |
| 5,658,995 | Copolymers of tyrosine-based polycarbonate and poly(alkylene oxide) | Random block copolymer of a tyrosine-derived diphenol monomer and a poly(alkylene oxide) synthesis |
| 6,048,521 | Copolymers of tyrosine-based polyarlates and poly(alkylene oxides) | Random block copolymers of both polycarbonates and polyarylates with and poly(alkylene oxides) |
| 6,120,491 | Biodegradable, anionic polymers derived from the amino acid L-tyrosine | Synthesis of block copolymers of polycarbonates and polyarylates having pendent carboxylic acid groups with poly(alkylene oxides) groups in the backbone. |
| 6,284,862 | Monomers derived from hydroxy acids and polymers prepared therefrom | Synthesis of aliphatic-aromatic dihydroxy monomers and bioresorbable polymers |
| 4,863,735 | Biodegradable polymeric drug delivery system with adjuvant activity | Poly(iminocarbonate) synthesis |
| 6,238,687 | Biodegradable polymers, compositions, articles and methods for making and using the same | Processes for preparing phosphorus and desaminotyrosyl L-tyrosine linkages in the polymer backbone |
| 5,912,225 | Biodegradable poly (phosphoester-co-desaminotyrosyl L-tyrosine ester) compounds, compositions, articles and methods for making and using the same | Processes for preparing polymers containing phosphorus and desaminotyrosyl L-tyrosine linkages |
| 4,638,045 | Non-peptide polyamino acid bioerodible polymers | Polymers with a plurality of monomer units of two or three amino acids |
| 6,602,497 | Strictly alternating poly(alkylene oxide ether) copolymers | Polyethers with strictly alternating poly(alkylene oxide) and tyrosine-derived monomeric repeating units |
| 5,198,507 | Synthesis of Amino Acid-derived bioerodible polymers | Polymer blends of the amino acid-derived polycarbonates with polyiminocarbonates prepared from identical amino acid-derived diphenol starting materials |

All of the U.S. Patents recited in TABLE 1 and their methods of preparation are incorporated herein in their entirety by reference thereto. The polyethers of U.S. Pat. No. 6,602,497 may require cross-linking before use in embolotherapy. However, appropriate cross-linking methods are essentially conventional and require no undue experimentation on the part of the ordinarily skilled artisan.

The term, "ortho-directed", is used herein to designate orientation relative to the phenoxy alcohol group.

The term, "inherently radiopaque", is used herein to designate polymer that is intrinsically radiopaque due to the covalent bonding of halogen species to the polymer. Accordingly, the term does not encompass a polymer, which is simply blended with a halogenated species or other radiopacifying agents such as metals and their complexes.

The halogenated compositional variations of the polymers in TABLE 1 may be generically represented by the following formulas. It should be noted that the compositional ranges noted below exceeds those described in TABLE 1.

It is understood that the presentation of the various polymer formulae represented may include homopolymers and heteropolymers, and also the stereoisomers thereof. Homopolymer is used herein to designate a polymer comprised of all the same type of monomers. Heteropolymer is used herein to designate a polymer comprised of two or more different types of monomer, which is also called a co-polymer. A heteropolymer or co-polymer may be of a kind known as block, random and alternating. Further with respect to the presentation of the various polymer formulae, embolotherapy products according to embodiments of the present invention may be comprised of a homopolymer, a heteropolymer and/or a blend of such polymers.

Preferred Polymers

In accordance with one preferred embodiment of the present invention, an embolotherapy product is disclosed, comprising an inherently radiopaque, biocompatible, bioresorbable polymer, including homogeneous polymers, copolymers and blends thereof, wherein the polymer comprises one or more of the following units (Formula I):

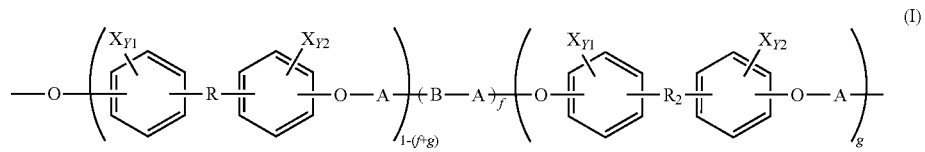

wherein X=I or Br; Y1 and Y2 can independently=0, 1, 2, 3 or 4;

wherein f and g can range from 0 to 1 as compositional/performance requirements dictate, provided that f is less than 1 and f+g is between 0 and 1, inclusive;

R and R₂ may be independently selected from:

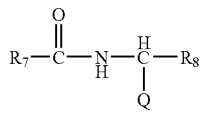

wherein $R_7$ is selected from the group consisting of —CH=CH—, —CHJ₁-CHJ₂- and (—CH₂—)a, wherein $R_8$ is selected from the group consisting of —CH=CH—, —CHJ₁-CHJ₂- and (—CH₂—)n, wherein a and n are independently between 0 and 8 inclusive; and $J_1$ and $J_2$ are independently Br or I; and Q for each $R_2$ comprises a free carboxylic acid group, and Q for each R is selected from the group consisting of hydrogen, and carboxylic acid esters and amides, wherein said esters and amides are selected from the group consisting of esters and amides of alkyl and alkylaryl groups containing up to 18 carbon atoms and esters and amides of biologically and pharmaceutically active compounds.

In more preferred embodiments of Formula I, R and $R_2$ may be independently selected from the groups:

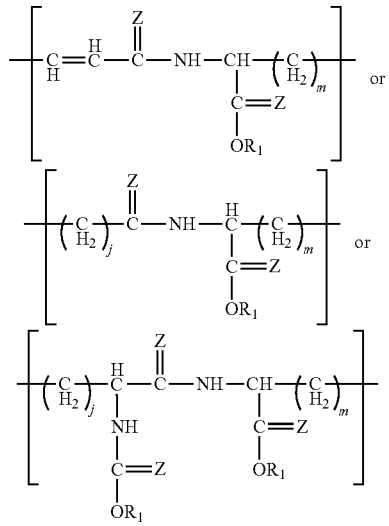

wherein $R_1$ for each $R_2$ is H and $R_1$ for each R is independently a long chain aliphatic hydrocarbon, and in some embodiments, an alkyl group ranging from 1 to about 18 carbon atoms containing from 0 to 5 heteroatoms selected from O and N;

wherein j and m are independently integers from 1 to 8 inclusive;

wherein Z is independently either O or S;

A is either:

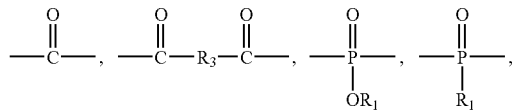

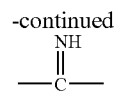

wherein $R_1$ is defined as previously;

wherein $R_3$ is a saturated or unsaturated, substituted or unsubstituted alkyl, aryl, or alkylaryl group containing up to about 18 carbon atoms and 0 to 8 heteroatoms selected from O and N; and wherein B is an aliphatic linear or branched diol or a poly(alkylene glycol) unit.

According to one embodiment of the invention, a product is provided in which the inherently radiopaque, biocompatible, bioresorbable polymer contains one or more units described by Formula II:

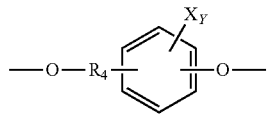

wherein X for each polymer unit is independently Br or I, Y is between 1 and 4, inclusive, and $R_4$ is an alkyl, aryl or alkylaryl group with up to 18 carbon atoms and from 0 to 8 heteroatoms selected from O and N.

When $R_4$ is an alkyl, it preferably has the structure:

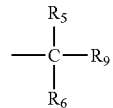

wherein $R_9$ for each unit is independently an alkyl, aryl or alkylaryl group containing up to 18 carbon atoms and from 0 to 8 heteroatoms selected from O and N; and $R_5$ and $R_6$ are each independently selected from hydrogen and alkyl groups having up to 18 carbon atoms and from 0 to 8 heteroatoms selected from O and N.

Each $R_9$ preferably contains a pendant $COOR_1$ group, wherein the subgroup $R_1$ is as defined previously. In one embodiment, $R_9$ is:

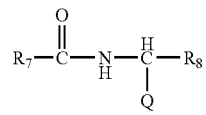

wherein $R_7$ is selected from the group consisting of —CH=CH—, —CHJ₁-CHJ₂- and (—CH₂—)a, wherein $R_8$ is selected from the group consisting of —CH=CH—, —CHJ₁-CHJ₂- and (—CH₂—)n, wherein a and n are independently between 0 and 8 inclusive; and $J_1$ and $J_2$ are independently Br or I; and Q is selected from the group consisting of hydrogen, a free carboxylic acid group, and carboxylic acid esters and amides, wherein said esters and amides are selected from the group consisting of esters and amides of alkyl and alkylaryl groups containing up to 18 carbon atoms and esters and amides of biologically and pharmaceutically active compounds.

More preferably, each $R_9$ independently has the structure:

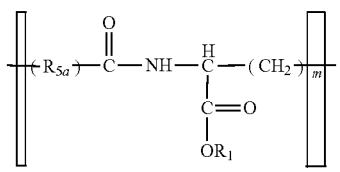

wherein $R_{5a}$ is defined as previously, and the COO $R_1$ group is as described herein for; and wherein m is an integer from 1 to 8 inclusive.

In another preferred embodiment, $R_9$ is:

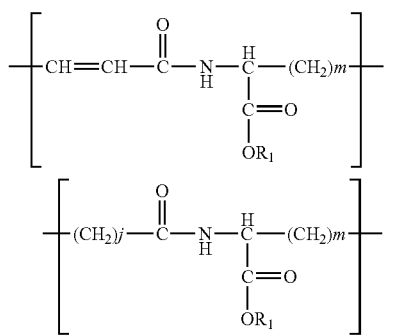

wherein j and m are independently an integer from 1 to 8, inclusive, and the $COOR_1$ group is as described herein for $R_9$.

Preferred polymer embodiments containing $R_4$ aryl or alkylaryl species are selected so that the unit described by Formula II is a diphenol.

In another preferred embodiment of the present invention, diphenolic polymers may comprise one or more diphenol units described by Formula III:

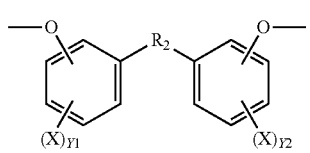

wherein X and $R_2$ are the same as described herein with respect to Formulas I and II, Y1 and Y2 are independently between 0 and 4, inclusive, and Y1+Y2 is between 1 and 8, inclusive.

In a more preferred version of this polymer embodiment, the diphenolic polymer comprises one or more units described by Formula IV:

wherein each X is independently I or Br, Y1 and Y2 for each diphenol unit are independently between 0 and 4, inclusive, and Y1+Y2 for each diphenol unit is between 1 and 8, inclusive;

each R and $R_2$ are independently an alkyl, aryl or alkylaryl group containing up to 18 carbon atoms and from 0 to 8 heteroatoms selected from O and N, wherein $R_2$ further includes a pendant carboxylic acid group;

A is either:

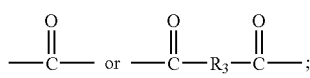

wherein $R_3$ is a saturated or unsaturated, substituted or unsubstituted alkyl, aryl, or alkylaryl group containing up to about 18 carbon atoms and 0 to 8 heteroatoms selected from O and N; P is a poly($C_1$-$C_4$ alkylene glycol) unit; f is between 0 and less than 1, inclusive; g is between 0 and 1, inclusive, f+g is between 0 and 1, inclusive; and the weight fraction of the poly(alkylene glycol) is about 75% or less. P is preferably a poly (ethylene glycol) that is present in a weight fraction of about 50% or less, and more preferably about 30% or less.

R and $R_2$ preferably each contain a pendant $COOR_1$ group, wherein for R, the subgroup $R_1$ is independently an alkyl group ranging from 1 to about 18 carbon atoms containing from 0 to 5 heteroatoms selected from O and N, and, for $R_2$, the subgroup $R_1$ is a hydrogen atom.

In one preferred embodiment, each R and $R_2$ independently has the structure:

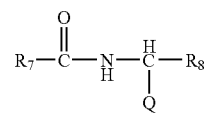

wherein $R_7$ is selected from the group consisting of —CH=CH—, —$CHJ_1$-$CHJ_2$- and (—$CH_2$—)a, wherein $R_8$ is selected from the group consisting of —CH=CH—, —$CHJ_1$-$CHJ_2$- and (—$CH_2$—)n, wherein a and n are independently between 0 and 8 inclusive; and $J_1$ and $J_2$ are independently Br or I; and, for each $R_2$, Q comprises a free carboxylic acid group, and, for each R, Q is independently selected from the group consisting of hydrogen and carboxylic acid esters and amides, wherein said esters and amides are selected from the group consisting of esters and amides of alkyl and alkylaryl groups containing up to 18 carbon atoms and esters and amides of biologically and pharmaceutically active compounds.

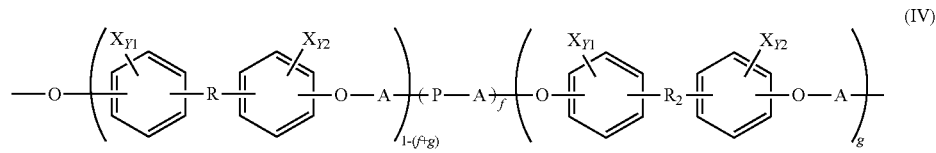

More preferably, each R and $R_2$ independently has the structure:

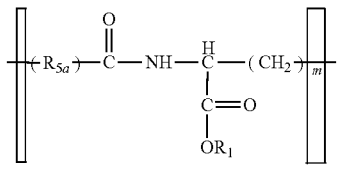

wherein $R_{5a}$ is defined as previously with regard to Formula II, and the $COOR_1$ group is as described herein for R and $R_2$. In a more preferred embodiment, R and $R_2$ species may be selected from:

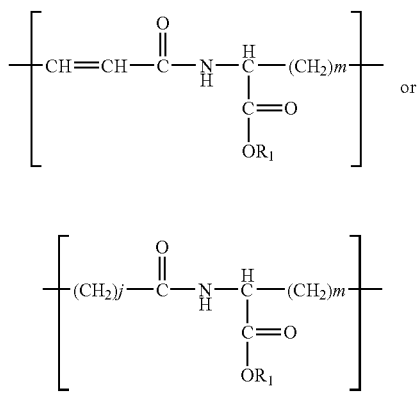

wherein j and m are independently an integer from 1 to 8, inclusive, and the and the $COOR_1$ group is as described herein for R and $R_2$.

In another variation to the polymer, each $R_1$ subgroup for R is ethyl or butyl.

In another embodiment, A is —C(=O)—.

In another embodiment, A is:

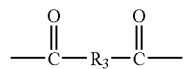

wherein $R_3$ is a saturated or unsaturated, substituted or unsubstituted alkyl, aryl, or alkylaryl group containing up to about 18 carbon atoms and 0 to 8 heteroatoms selected from O and N, and more preferably $C_4$-$C_{12}$ alkyl, $C_8$-$C_{14}$ aryl, or $C_8$-$C_{14}$ alkylaryl. In another preferred embodiment, $R_3$ may be selected from —CH2-C(=O)—, —CH2-CH2-C(=O)—, —CH=CH— and (—CH2—)z, wherein z is an integer from 0 to 8, inclusive.

Polymers according to the present invention include embodiments in which iodine and bromine are both present as ring substituents.

According to another aspect of the preferred embodiments, an embolotherapy product is provided, formed from a ring-substituted polymer containing one or more units described by Formula V:

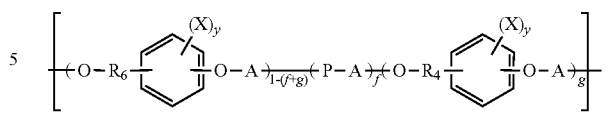

wherein each X is independently iodine or bromine; each y is independently 1 or 2; each $R_4$ and $R_6$ are independently an alkyl, aryl or alkylaryl group containing up to 18 carbon atoms and from 0 to 8 heteroatoms selected from O and N; and A, P, f and g are the same as described above with respect to Formula IV.

$R_4$ and $R_6$ preferably each contain a pendant $COOR_1$ group, wherein for $R_6$, the subgroup $R_1$ is independently an alkyl group ranging from 1 to about 18 carbon atoms containing from 0 to 5 heteroatoms selected from O or N, and, for $R_4$, the subgroup $R_1$ is a hydrogen atom. More preferably, each $R_4$ and $R_6$ is:

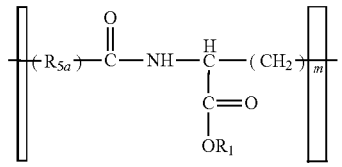

wherein $R_{5a}$ is defined as previously with regard to Formula II, and the $COOR_1$ group is as described herein for $R_4$ and $R_6$.

It is understood that the presentation of the various polymer formulae is schematic and that the Formulae IV and V polymer structures represented are random copolymers with respect to the position of P so that the different subunits can occur in random sequence throughout the polymeric backbone. In most cases, A is connected to either P or a phenolic ring.

Typically, P is a poly(alkylene glycol) unit having a molecular weight of about 10,000 or less, and more typically, about 4000 or less. P is preferably a poly(ethylene glycol) unit having a molecular weight between about 1000 and about 2000.

When A is a carbonyl (C=O), the Formula IV polymers of the preferred embodiments comprise polycarbonates and the Formula V polymers comprise poly(amide carbonates). When A is:

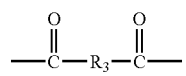

the Formula IV polymers of the preferred embodiments comprise polyarylates and the Formula V polymers comprise poly(ester amides).

In embodiments wherein Formula IV defines a polyarylate and Formula V defines a poly(ester amide), $R_3$ is a saturated or unsaturated, substituted or unsubstituted alkyl, aryl, or alkylaryl group containing up to about 18 carbon atoms and from 0 to 8 heteroatoms selected from O and N. In preferred embodiments, $R_3$ is an alkyl group containing between about 2 and about 12 carbon atoms. In some preferred embodiments, $R_3$ is either a straight or branched chain alkyl group. In more preferred embodiments, the $R_3$ group is —$CH_2$—

$-CH_2-$, $-CH_2-CH_2-CH_2-CH_2-$ or $-CH_2-CH_2-CH_2-CH_2-CH_2-CH_2-$. The $R_3$ groups can be substituted with any suitable functional group that, preferably, does not or tends not, to cross-react with other monomeric compounds during polymerization or otherwise interfere significantly with the formation of the present polymers via polymerization as described below. In cases where cross reaction can occur, one skilled in the art can utilize methods, such as use of protecting groups or other methods known in the art, to obtain a preferred compound.

In certain preferred embodiments, $R_3$ is selected such that the A-moieties in Formulae IV and V are derived from dicarboxylic acids that are naturally occurring metabolites or highly biocompatible compounds. For example, in some embodiments, $R_3$ is selected such that the polyarylate A-moieties in Formula III are derived from the intermediate dicarboxylic acids of the cellular respiration pathway known as the Krebs Cycle. Such dicarboxylic acids include sebacic acid, adipic acid, oxalic acid, malonic acid, glutaric acid, pimelic acid, suberic acid and azelaic acid. Accordingly, $R_3$ is more preferably a moiety selected from $-CH=CH-$ and $(-CH_2-)_z$, wherein z is an integer from 0 to 8, and preferably from 4 to 8, inclusive.

In certain embodiments, X in Formulae IV and V is preferably iodine. In certain embodiments, when present, P in Formulae IV and V is preferably a poly(ethylene glycol) unit. In Formulae IV and V, f preferably ranges from greater than 0.1 to about 0.3 inclusive, and more preferably from greater than 0.2 to about 0.25 when present. As illustrated in Formulae IV and V, and unless otherwise indicated, the molar fractions reported are based on the total molar amount of dicarboxylic acid or $-C(=O)-$ units, carboxylic acid ester monomeric units, free carboxylic acid units, and poly(alkylene glycol) units in the polymeric units of Formulae IV and V.

Applicants have recognized that the molar fraction of free carboxylic acid units, such as desaminotyrosyl tyrosine (DT) units, in the polymers of the preferred embodiments can be adjusted to likewise adjust the degradation/resorbability of the embolotherapy compositions of the present invention. For example, applicants have recognized that polymers comprising about 35% free carboxylic acid units (a molar fraction of about 0.35) are about 90% resorbed in about 15 days, which may be clinically desirable for embolotherapy agents. Stated another way, the higher the molar fraction of carboxylic acid units, the shorter the lifetime of the embolotherapy agents in the body. In certain embodiments where lifetimes of the embolotherapy agents from several weeks to several months are required, polymers having a range of "g" values from about 0.2 to about 0.3 tend to be desirable. According to preferred embodiments, the molar fraction, g, of repeating units in Formulae IV and V derived from carboxylic acid units ranges from greater than about 0.1 to about 0.3 inclusive, preferably from greater than about 0.2 to about 0.3. However, the present invention also includes slowly-resorbing compositions and devices prepared from polymers in which g=0.

In certain preferred embodiments for embolotherapy agents, the copolymers employed have weight-average molecular weights (Mw) of from about 20,000 to about 200,000, preferably from about 50,000 to about 150,000, and more preferably from about 75,000 to about 100,000. The polydispersity ($P_d$) values of the copolymers are in the range of about 1.5 to about 2.5 and are usually about 2. The corresponding number-average molecular weights (Mn) of the copolymers for embolotherapy agents can be calculated as described above and will be from about 10,000 to about 100,000, more preferably from about 25,000 to about 75,000, and even more preferably from about 37,500 to about 50,000.

The molecular weights are measured by gel permeation chromatography (GPC) relative to polystyrene standards without further correction.

Methods of Manufacture

The embolotherapy polymers of Formula IV can be prepared via any of a variety of methods. As noted above, the polymers described by Formula IV optionally include ring-substituted diphenolic polycarbonates or polyarylates comprising diphenolic acid ester units with pendant $COOR_1$ groups, diphenolic units with pendant COOH groups, and poly(alkylene glycol) units in the defined relative amounts. Accordingly, the free carboxylic acid group polymers are prepared by methods comprising polymerizing a desired ratio of poly(alkylene glycol)s and one or more ring-substituted diphenol monomer compounds (including an amount of monomer compounds with pendant $COOR_1$ groups for which the subgroup $R_1$ is a protecting group, preferably a tert-butyl ester group, in a stoichiometrically quantity equivalent to the molar fraction of pendant COOH groups desired), followed by a deprotection reaction to remove the tert-butyl ester protecting groups to form the pendant COOH groups.

The Formulae V poly(amide carbonates) and poly(ester amides) are similarly polymerized from a desired ratio of poly(alkylene glycol) and ring-substituted aliphatic-aromatic dihydroxy acid ester units with pendant $COOR_1$ groups (including an amount of monomer compounds with pendant $COOR_1$ groups for which the subgroup $R_1$ is a protecting group, preferably a tert-butyl ester group, in a stoichiometrically quantity equivalent to the molar fraction of pendant $-COOH$ groups desired), and then deprotected.

Examples of methods adaptable for use to prepare polycarbonate or polyarylate polymers of the preferred embodiments are disclosed in U.S. Pat. Nos. 5,099,060, 5,587,507, 5,658,995, 5,670,602, 6,120,491, and 6,475,477 the disclosures of which are incorporated herein by reference. Other suitable processes, associated catalysts and solvents are known in the art and are taught in Schnell, Chemistry and Physics of Polycarbonates, (Interscience, New York 1964), the teachings of which are incorporated herein by reference.

Polycarbonates can also be produced using the novel polymerization method disclosed in the co-pending, commonly owned U.S. Patent Application 60/601,743 filed by Joachim B. Kohn, Durgadas Bolikal, Aaron F. Pesnell, Joan Zeltinger, Donald K. Brandom and Eric Schmid on Aug. 13, 2004 entitled "Radiopaque Polymeric Medical Devices," the disclosure of which is incorporated in its entirety by reference. Briefly, the method comprises dissolving the diphenol monomers and polyethylene glycol in methylene chloride containing 0.1M pyridine or triethylamine. A solution of phosgene in toluene is then added at a constant rate, followed by quenching and work up of the polymer. Residual pyridine (if used) is then removed by agitation of a tetrahydrofuran (THF) polymer solution with a strongly acidic resin, such as AMBERLYST™ 15. This method can be widely applied to any polycarbonate of Formula II.

Methods for preparing diphenol monomers for use in making the present polymers are disclosed, for example, in U.S. Pat. Nos. 5,587,507, and 5,670,602. In particular, such references disclose the preparation of non-ester desaminotyrosyl-tyrosine free carboxylic acid (DT), as well as, desaminotyrosyl-tyrosine esters, including the ethyl (DTE), butyl (DTB), hexyl (DTH), octyl (DTO), benzyl (DTBn), and other esters. Iodine- and bromine-substituted diphenol monomers can be prepared, for example, by coupling together, via any of the procedures disclosed herein, two phenol compounds in which either or both of the phenol rings are iodine or bromine substituted, or forming a diphenol that is iodinated or brominated after coupling via any suitable iodination or bromination method.

Methods for preparing the Formula V poly(ester amides) and poly(amide carbonates), and the aliphatic-aromatic dihydroxy monomers from which they are polymerized, including ring-iodinated or brominated monomers, are described in U.S. Pat. No. 6,284,862, the disclosure of which is incorporated by reference. The disclosed poly(amide carbonate) polymerization process can be adapted to use the above-discussed process in which a toluene solution of phosgene replaces bubbling gaseous phosgene through a monomer solution.

While any of the aforementioned processes are adaptable for use herein, preparation of the polycarbonates, polyarylates, poly(ester amides) and poly(amide carbonates) of the preferred embodiments having pendant free carboxylic acid groups from monomers having free carboxylic acid groups (such as DT monomers) can occur with cross-reaction of the monomer carboxylic acid groups with co-monomers. Accordingly, in certain preferred embodiments, the polymers of the preferred embodiments are prepared by polymerizing iodine or bromine ring substituted alkyl ester monomers with poly(alkylene glycols) and temporarily protected free acid monomers (monomers wherein the free acid functionality is masked using a temporary protecting group), which may also have iodine or bromine ring-substituents, to form a polycarbonate, polyarylate, poly(ester amide) or poly(amide carbonate) polymeric unit from which the temporary protecting groups are selectively removable to produce the corresponding free carboxylic acid groups. This method can be widely applied to any polymer of Formula II for which a pendant free carboxylic acid group is intended.

Any of a wide variety of suitable protection/deprotection methods can be adapted for use in the preparation of the polymeric devices of the preferred embodiments, including the methods for converting DTBn moieties to DT moieties as described, for example, in U.S. Pat. No. 6,120,491, incorporated herein by reference. A similar method by which poly(ester amides) and poly(amide carbonates) with free carboxylic acid groups are prepared by the hydrogenolysis of corresponding benzyl ester copolymers is described in the aforementioned U.S. Pat. No. 6,284,862. In other words, the method of U.S. Pat. No. 6,120,491 can be extended to any polymer of Formula II for which a pendant free carboxylic acid group is intended. In preferred embodiments, the polymers of the preferred embodiments, are produced using the novel deprotection method of the commonly owned U.S. Patent Application 60/601,743 filed by Joachim B. Kohn, Durgadas Bolikal, Aaron F. Pesnell, Joan Zeltinger, Donald K. Brandom and Eric Schmid on Aug. 13, 2004 entitled "Radiopaque Polymeric Medical Devices." T-butyl ester protecting groups on hydrolytically unstable polymers are selectively removed to provide new polymers with free carboxylic acid groups in place of the t-butyl ester groups.

The polymer is contacted with the acid by dissolving the polymer in a suitable solvent containing an effective amount of the acid. Any suitable inert solvent in which the polymer to be deprotected is soluble can be used in the reaction mixture of the providing step of the present method. Examples of suitable solvents include, but are not limited to, chloroform, methylene chloride, THF, dimethylformamide, and the like. In certain preferred embodiments, the solvent comprises methylene chloride.

Any suitable weak acid capable of facilitating the selective removal of a t-butyl protecting group from the carboxylic acid group of a provided polymer by acidolysis can be used according to the present method. Examples of certain suitable weak acids include acids having a $pK_a$ of from about 0 to about 4, including formic acid, trifluoroacetic acid, chloroacetic acid, and the like. In certain preferred embodiments the weak acid is trifluoroacetic acid.

The amount of weak acid used should be the maximum quantity that can be added to the solvent without interfering with polymer solubility. The weak acid can serve as the solvent for polymers soluble therein. In this embodiment, a preferred acid is formic acid.

The contacting step, or portions thereof, can be conducted under any suitable conditions effective to selectively remove t-butyl protecting groups via acidolysis. Those of skill in the art will be readily able to adapt any of the wide range of acidolysis methods for use in the contacting step of the preferred embodiments to selectively remove t-butyl groups without undue experimentation. For example, in certain preferred embodiments, the contacting step is conducted at about 25° C. and about 1 atm.

In light of the disclosure herein, those of skill in the art will be readily able to produce a variety of hydrolytically unstable polymers with free carboxylic acid groups, and especially polymers of the preferred embodiments, for instance, for use in a variety of medical devices, from corresponding polymers comprising t-butyl protected free carboxylic acid repeating units.

After polymerization and deprotection, appropriate workup of the polymers of the preferred embodiments can be achieved by any of a variety of known methods to produce embolotherapy compositions and devices for use in the methods of the preferred embodiments. For example, in certain preferred embodiments, the polymers are shaped into particles suitable for use in compositions for embolizing or occluding a body lumen, preferably a blood vessel. Examples of preferred particles include, but are not limited to, spherical particles, geometrically non-uniform particles, porous particles, solid particles, hollow particles, and particles having an excluded diameter in the range of about 10 to about 3000 microns and more preferably in the range of about 40 to 2,400 microns. In other embolotherapy products, the polymers may be formed into hydrogels for use in embolizing or occluding a body lumen.

Any of a variety of conventional methods for producing polymeric particles, hydrogels, and the like can be adapted for use in the preferred embodiments. In light of the disclosure herein, those of skill in the art will be readily able to produce the embolotherapy products of the preferred embodiments without undue experimentation.

Polymer particles, for example, are typically prepared by adding a dilute solution (about 5 wt %) of polymer in a solvent for the polymer, such as dimethyl sulfoxide (DMSO), through a narrow gauge needle to a volume of water containing an appropriate surfactant. The needle gauge selected will determine the polymer particle size. The precipitated polymer spheres are isolated by filtration through a drop funnel and permitted to air dry, followed by cryogenic grinding and drying under vacuum at an elevated temperature selected to prevent the formation of agglomerates (about 50° C.).

One of ordinary skill in the art can adapt the polymers used in the preferred embodiments to the known processes for producing embolotherapy polymer particles without undue experimentation. Particle size ranges will vary depending upon the embolotherapy indication. Polymer particle sizes are typically in the range of about 10 to 3000 microns, and more typically grouped as follows: about 45 to about 90 microns (μm), about 90 to about 190 μm, about 190 to about 300 μm, about 300 to about 500 μm, about 500 to about 710

μm, about 710 to about 1,000 μm, about 1,000 to about 1,400 μm, about 1,400 to about 2,000 μm, about 2,000 to about 2,400 μm and about 2,400 to about 3,000 μm.

The PEG-containing polymers used in the preferred embodiments have been discovered to have surface properties well-suited for passage through a narrow gauge needle to form micron-sized particles.

Polymer Formulations

In another preferred embodiment of the above-described products and methods, the polymers are formulated with an effective amount of at least one magnetic resonance enhancing agent. In yet another preferred embodiment of the above-described products and methods, the polymers are formulated with effective amounts of at least one therapeutic agent and at least one magnetic resonance enhancing agent. In yet another preferred embodiment of the above-described products and methods, the polymers are formulated with a radiopacifying agent for instance, but not limited to iodine, bromine, barium, bismuth, gold, platinum, tantalum, tungsten, and mixtures thereof.

In preferred aspects, the inherently radiopaque, biocompatible, bioresorbable polymers may be made in the form of spherical particles. In the alternative, the polymers may be made in the form of geometrically non-uniform particles. Either spherical or geometrically non-uniform particles may be hydrogel in character wherein the particles are porous, solid or hollow. The particles may have an excluded diameter in the range of about 10 to about 5000 microns, preferably about 40 to 3000 microns and more preferably about 45 to 2,400 microns. The particles may incorporate one or more of the above-disclosed therapeutic agents, magnetic resonance enhancing agents and radiopacifying agents.

Examples of preferred magnetic resonance enhancing agents include, but are not limited to, gadolinium salts such as gadolinium carbonate, gadolinium oxide, gadolinium chloride, mixtures thereof, and the like. In compositions and devices containing a magnetic resonance enhancing agent, an amount of magnetic resonance enhancing agent sufficient for radiologic imaging is used, which can again be determined by one of ordinary skill in the art without undue experimentation.

In certain embodiments, the embolotherapy compositions and devices of the preferred embodiments further comprise radio-opacifying agents. In certain embodiments, embolotherapy compositions and devices also comprise compositions and devices formed from non-iodinated and non-brominated analogs of the Formula II polymers to which a radio-opacifying agent has been added. Preferred embodiments can include Formula II polymers as such compound analogs. Radio-opacifying agents can be added to the Formula II polymers to enhance their radio-opacity. Examples of preferred radio-opacifying agents include, but are not limited to, iodine metal, organic iodine compounds, bromine, barium sulfate, bismuth oxide, gold, platinum, tantalum, tungsten, mixtures thereof, and the like.

Embolotherapy Methods

According to another aspect of the preferred embodiments, methods are disclosed for embolizing a body lumen by introducing into the body lumen an effective amount of an embolotherapy product prepared from the inherently radiopaque, biocompatible, bioresorbable polymers disclosed herein.

In another preferred embodiment of the above-described products, a resorbing inherently radiopaque composition of biocompatible embolic particles may be formulated for the specific treatment and re-treatment of cancerous tumors. A resorbing formula will allow for the multiple chemotherapeutic treatments. Moreover, the flexible chemistry of the preferred embolotherapy products allows tuning of the resorption profile, such that residence time within the vessels can be readily modified by changing the polymer structure—as detailed below. For example, embolic particles of the present invention, chemically formulated to resorb could be implanted in conjunction with a chemotherapeutic agent in order to restrict application of the chemotherapeutic agent to the cancerous tissue. Such a concentrated attack on the cancer cells would be particularly desired for example in the case of hepatic carcinoma. The chemotherapeutic agent could be on the particles, in the particles and/or bonded to the particle polymer and/or introduced with the polymer as in a delivery solution. In this fashion the agent may have its therapeutic effect. Upon resorption of the embolic agent and recanalization of the vessels, the process could then be repeated. The inherently radiopaque particles allows more controlled delivery not only of the particles but also the therapeutic, and allows for multiple treatment approach, which is not currently possible and represents a significant unmet therapeutic need.

Thus, according to another aspect of the preferred embodiments, methods are disclosed for enhancing the local delivery of a therapeutic agent to a tissue by (1) administering to a blood vessel associated with the tissue an amount of an embolotherapy product prepared from the inherently radiopaque, biocompatible, bioresorbable polymers disclosed herein sufficient to reduce the blood flow from the tissue; (2) administering the therapeutic agent to the blood vessel separately or in combination with the embolotherapy product, so that the local delivery of the therapeutic agent is enhanced; and (3) repeating the steps of administering the embolotherapy product and therapeutic agent after the embolotherapy product first administered has degraded sufficiently to allow for re-access to said blood vessel.

In accordance with another preferred embodiment of the present invention, a method is disclosed for embolizing a body lumen. The method comprises introducing into the body lumen an effective amount of a composition, comprising a biocompatible, bioresorbable polymer, wherein the polymer comprises a radiopaque moiety selected from the group consisting of iodine, bromine, barium, bismuth, gold, platinum, tantalum, tungsten and mixtures thereof. More preferably, the method comprises the step of introducing into a blood vessel an embolotherapy particle comprising a biocompatible, bioresorbable polymer comprising sufficient halogen atoms to render the particle radiopaque.

In certain embodiments these bioresorbable, inherently radiopaque embolic agents may be delivered by the conventional delivery system such as a guide catheter when embolizing tumors, vascular malformations (e.g., for uterine fibroids, tumors (i.e., chemo-embolization), hemorrhage (e.g., during trauma with bleeding) and arteriovenous malformations, fistulas and aneurysms. In another embodiment these bioresorbable, inherently radiopaque embolic agents may be delivered by less conventional delivery systems, for example, direct injection into a body lumen via a syringe or other non-catheter system to provide cosmetic treatment for spider veins and/or varicose veins. Indeed, where direct injection into surface veins is undertaken, the polymeric embolotherapy product may not need to be radiopaque. Accordingly, for applications such as cosmetic treatment for spider veins and/or varicose veins, non-halogenated polymers in accordance with certain embodiments of the present invention may be used with efficacy. The addition and/or polymer-based delivery of therapeutic agents may also be advantageously used for such cosmetic clinical indications.

The preferred embodiments further provide methods for embolizing a body lumen comprising introducing into the body lumen an embolizing composition prepared from a polymer of Formula II. According to certain preferred embodiments, effective amounts of compositions are employed containing one or more of the following: spherical particles, geometrically non-uniform particles, porous particles, solid particles, hollow particles, particles having an excluded diameter in the range of about 10 to about 3000 microns and more preferably from about 40 to about 2,400 microns, hydrogels, and any combinations thereof. Any suitable conventional methods for introducing an embolotherapy composition to a body lumen for embolizing the body lumen can be adapted for use in the preferred embodiments. For example, traditional methods for introducing PVA embolics to a body lumen can be used with substituting the compositions of the preferred embodiments for the PVA embolics.

Therapeutic Agents

According to a preferred embodiment of the above-described embolotherapy products and methods, the polymers may be formulated with an effective amount of at least one therapeutic agent (e.g., a pharmaceutical agent and/or biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biologic agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biologic agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

The amount of the therapeutic agent is preferably sufficient to perform as, but not limited to, a chemotherapeutic agent, non-steroidal anti-inflammatory agent, and/or steroidal anti-inflammatory agent to promote a desirable biological and/or physiological response or to affect some other state of the embolized tissue, for instance, attract healing cells or those that produce extracellular matrix to aid healing of the embolized body lumen.

Therapeutic agents can be incorporated onto the embolotherapy product on at least one region of the surface, or in some cases in the product, thereby providing local release of such agents. In some preferred embodiments, the therapeutic agent is delivered from a thin polymer coating or other carrier on the particle surface. In another preferred variation, the therapeutic agent is delivered by means of a polymer coating. In other preferred embodiments of the embolotherapy product, the therapeutic agent is delivered from at least one region or one surface of the embolotherapy product. In other preferred embodiments of the embolotherapy product, the therapeutic agent is contained within the embolotherapy product as the agent is blended with the polymer or admixed by other means known to those skilled in the art. In other preferred embodiments, the therapeutic agent can be chemically bonded to a polymer or other carrier used to coat the particles and/or bonded to at least one portion of the particle polymer and/or bonded to the particle polymer indirectly by means of a separate linker or ligand. In another variation, the embolotherapy product may comprise more than one therapeutic agent, for example, coated on at least a portion of the particle surface, admixed within the polymeric matrix, etc.

In another preferred embodiment of the above-described products and methods, the embolotherapy product may be formulated with an effective amount of a coating that is a biocompatible, bioresorbable coating sufficient to promote a desirable biological and/or physiological effect.

In certain embodiments, the embolotherapy compositions and devices of the preferred embodiments further comprise therapeutic agents (e.g., a pharmaceutical agent and/or biologic agent) as previously defined herein and/or magnetic resonance enhancing agents. The amount of the therapeutic agent is preferably sufficient to perform as, but not limited to, a chemotherapeutic agent, non-steroidal anti-inflammatory agent, and/or steroidal anti-inflammatory agent to promote a desirable biological and/or physiological response or to affect some other state of the embolized tissue, for instance, attract healing cells or those that produce extracellular matrix to aid healing.

Therapeutic agents can be incorporated onto the embolotherapy product on at least one region of the surface, or in some cases in the product, thereby providing local release of such agents. In some preferred embodiments, the therapeutic agent is delivered from a thin polymer coating on the polymeric particle surface. In another preferred variation, the therapeutic agent is delivered by means of no polymer coating. In other preferred embodiments of the embolotherapy product, the therapeutic agent is delivered from at least one region or one surface of the embolotherapy product. In other preferred embodiments of the embolotherapy product, the therapeutic agent is contained within the embolotherapy product as the agent is blended with the polymer or admixed by other means known to those skilled in the art.

The therapeutic agents in accordance with preferred aspects of the invention may be classified in terms of their sites of action in the host, for example they may exert their actions extracellularly or at specific membrane receptor sites, at the plasma membrane, within the cytoplasm, and in the nucleus. Therapeutic agents may be polar or possess a net negative or positive or neutral charge; they may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

Examples of suitable therapeutic agents include, but are not limited to, chemotherapeutic agents, non-steroidal anti-inflammatory agents, steroidal anti-inflammatory agents. Examples of preferred chemotherapeutic agents include, but are not limited to, taxanes, taxinines, taxols, paclitaxel, dioxorubicin, cis-platin, adriamycin, bleomycin, and the like. Examples of preferred non-steroidal anti-inflammatory compounds include, but are not limited to, aspirin, dexamethasone, ibuprofen, naproxen, Cox-2 inhibitors, such as Rofexcoxib, Celecoxib and Valdecoxib, and the like. Examples of preferred steroidal anti-inflammatory compounds include, but are not limited to, dexamethasone, beclomethasone, hydrocortisone, prednisone, and the like.

Any suitable amount of one or more therapeutic agents may be used. Preferably, an amount of therapeutic agent effective to have a local therapeutic effect is employed, which can be readily determined by one of ordinary skill in the art without undue experimentation.

Embolotherapy Products Having Surface Coatings

In addition to embolotherapy products that may deliver a therapeutic agent, for instance delivery of a biological polymer on the product such as thrombogenic collagen or fibronectin or a repellant phosphorylcholine, the embolotherapy products may be delivered or coated with bioresorbable polymers predetermined to promote biological responses in the embolized body lumen desired for certain clinical effectiveness. Further the coating may be used to mask the surface properties of the polymer used to comprise the embolotherapy particles. The coating may be selected from the broad class of any non-halogenated or halogenated biocompatible bioresorbable polymer which may or may not comprise any poly(alkylene glycol). These polymers may include compositional variations including homopolymers and heteropolymers, stereoisomers and/or a blend of such polymers. These polymers may include for example, but are not limited to, polycarbonates, polyarylates, poly(ester amides), poly(amide carbonates), trimethylene carbonates, polycaprolactones, polydioxanes, polyhydroxybutyrates, polyhydroxyvalerates, polyglycolides, polylactides and stereoisomers and copolymers thereof, such as glycolide/lactide copolymers. In a preferred embodiment, the embolotherapy product is coated with a polymer that exhibits a high absorptive affinity for fibrinogen or plasma proteins to promote clot formation, for instance in the case of hemorrhage. For instance poly(DTE carbonate) and poly(I2DTE carbonate) promote high levels of fibrinogen adsorption; further a coating may comprise a polymer with a positive charge that attracts the negative charge of red blood cells' outer membranes thereby inducing a the body's normal clotting processes. In another preferred embodiment, the embolotherapy product is coated with a polymer that exhibits an affinity for cells, (e.g., mesenchymal, fibroblast, stromal cells and parenchymal) to promote healing and tissue resorption and remodeling of the embolized tissue, for instance in the case of treating uterine fibroids. In yet another preferred embodiment, the embolotherapy product is coated with a polymer that repels the attachment and/or proliferation of specific cells, for instance endothelial cells of microvessels known to vascularize a tumor; in this instance the polymer coating on the embolic product may slow down or inhibit further vascularization of an embolized tumor. In another preferred embodiment, the embolotherapy product is coated with a polymer that attracts cells and/or promotes their proliferation and/or deposition of extracellular matrix molecules that support formation of a reparative tissue (e.g., granulation tissue). This may include attraction of inflammatory cells such as macrophages that lead to successful healing and/or formation of fibroconnective tissue. In a preferred embodiment, the embolotherapy product is coated with a polymer that promotes tissue deposition as in the case of arteriovenous malformations and aneurysms.

The following non-limiting examples set forth below illustrate certain aspects of the invention. These examples are not intended to limit the scope, but rather to exemplify preferred embodiments. All parts and percentages are by weight unless otherwise noted and all temperatures are in degrees Celsius.

EXAMPLES

Nomenclature and Abbreviations Used

The following abbreviations are used to identify the various iodinated compounds. TE stands for tyrosine ethyl ester, DAT stands for desaminotyrosine and DTE for desaminotyrosyl tyrosine ethyl ester. The polymer obtained by phosgenation of DTE is denoted as poly(DTE carbonate). An "I" before the abbreviation shows mono-iodination (e.g. ITE stands for mono-iodinated TE) and an $I_2$ before the abbreviation shows di-iodination (e.g. $I_2$DAT stands for di-iodinated DAT). In DTE, if the "I" is before D, it means the iodine is on DAT and if "I" is after D, it means the iodine is on the tyrosine ring (e.g. $DI_2TE$ stands for DTE with 2 iodine atoms on the tyrosine ring). The following diagram illustrates this nomenclature further.

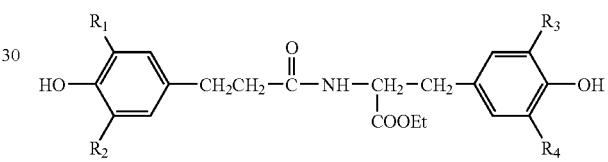

General Structure of Iodinated DTE Monomer $R_1=I, R_2, R_3, R_4=H; IDTE$ $R_1, R_2=I, R_3, R_4=H; I_2DTE$ $R_1, R_2=H, R_3, R_4=I; DI_2TE$ $R_1, R_3=I, R_2, R_4=H; IDITE$ Resorption Testing Polymer degradation rate was measured in vivo and in vitro using the materials and methods described in Abramson st al., "Small changes in polymer structure can dramatically increase degradation rates: the effect of free carboxylate groups on the properties of tyrosine-derived polycarbonates," *Sixth World Biomaterials Congress Transactions, Society for Biomaterials 26th Annual Meeting*, Abstract 1164 (2000), the disclosure of which is incorporated by reference.

Example 1

Preparation of Poly(60% $I_2$DTE-co-20% $I_2$DT-co-20% PEG2K Carbonate)

Into a three necked round-bottomed flask, equipped with a mechanical stirrer, a thermometer, a reflux condenser and a rubber septum were added 18.3 g (0.03 mol) of $I_2$DTE, 6.38 g (0.01 mol) of $I_2$DTtBu, 20 g (0.01 mol) of PEG2000, and 300 ml of methylene chloride. On stirring a clear light yellow solution was obtained. To this was added 15.1 ml (0.15 mol)

of pyridine. In a gas tight plastic syringe was placed 30 ml of a 20% solution of phosgene in toluene (0.0576 mol), which was added to the reaction flask over 3 h using a syringe pump. The molecular weight was determined by analyzing an aliquot of the reaction mixture by GPC. Additional phosgene solution (up to 10%) was needed to achieve desired molecular weight. The reaction mixture was quenched with 110 ml of THF and 10 ml of water. The polymer was precipitated by adding the reaction mixture to 1.5 L of cold 2-propanol in high speed Waring blender.

The resulting gluey polymer was ground with two portions of 0.5 L 2-propanol. The fine granular polymer particles were isolated by filtration and dried in a vacuum oven. To remove the t-Butyl protecting group, the polymer was dissolved in trifluoroacetic acid to obtain a 20% solution. After stirring the solution at room temperature for 4 h, the polymer was precipitated by adding to 2-propanol and then further grinding with 2-propanol to remove the excess TFA. The product was isolated by filtration, washed with IPA and dried in vacuum oven.

Those skilled in the art will recognize that radiopaque bromine-substituted polymers can be similarly prepared by replacing iodine with bromine in the starting materials.

Example 2

Preparation of Poly(I2DTE-co-2.5 mole % PEG2K Carbonate)

A polymer containing 97.5% mole percent $I_2$DTE and 2.5% poly(ethylene glycol) of molecular weight 2000 (poly (97.5% $I_2$DTE-co-2.5% PEG2K carbonate)) was prepared as follows. Into a three necked round-bottomed flask, equipped with a mechanical stirrer, a thermometer, a reflux condenser and a rubber septum, were added 29.7 g (0.0488 mol) of $I_2$DTE, 2.5 g (0.00125 mol) of PEG2000, and 215 ml of methylene chloride. On stirring a clear light yellow solution was obtained. To this was added 15.1 ml (0.15 mol) of pyridine. In a gas tight plastic syringe was placed 30 ml of a 20% solution of phosgene in toluene (0.0576 mol), which was added to the reaction flask over 3 h using a syringe pump. The molecular weight was determined by analyzing an aliquot of the reaction mixture by GPC. Additional phosgene solution (up to 10%) was added to achieve the desired molecular weight. The reaction mixture was quenched with 110 ml of tetrahydrofuran and 10 ml of water. The polymer was precipitated by adding the reaction mixture to 1.5 L of cold 2-propanol in high speed Waring blender. The resulting polymer was ground with two portions of 0.5 L 2-propanol. The fine granular polymer particles were isolated by filtration and dried in a vacuum oven.

Example 3

Formation of Embolotherapy Particles

A 5% w/w DMSO solution of the polymer of Example 2 was prepared by dissolving 0.650 g polymer in 12.35 g DMSO. A precipitation solution was prepared by adding 3 ml of a 10 vol % aqueous solution (from concentrate) of ALCONOX surfactant to 300 ml water. The precipitation solution was placed in a 600 ml container and stirred on a slow setting (<100 RPM). Adding the DMSO polymer solution to the precipitation solution in a drop-wise fashion from a syringe through a 26-gauge needle allows for polymer spheres to precipitate. The 26-gauge needle was ground to a point to buff off the silicone coating. This reduces surface tension, resulting in smaller drops of polymer when dispensed.

The precipitated polymer spheres were isolated through a filtered drop funnel and allowed to air dry. The spheres were then cryogenically ground in a coffee grinder at about 20,000 RPM with added $CO_2$. The ground particles were then dried overnight in a vacuum oven at 50° C. under dynamic vacuum. The dried spheres were then manually sieved into the following particle ranges:

90-180 micron diameter
180-300 micron diameter
300-500 micron diameter
500-710 micron diameter Example 4

In Vivo Evaluation or Particle Radio-Opacity

The acute radio-opacity of the embolotherapy particles of Example 3 was evaluated by injection into the renal arterial beds of a pig. The particles were injected via a catheter inserted into distal renal arterial beds.

Access to the renal arterial beds was achieved with a 5 F catheter over a 0.035" wire. A small profile catheter was advanced into the distal vascular bed to provide a more subselective injection. A baseline angiogram was taken on cine. The embolotherapy particles were mixed with saline in a beaker at about 5 cc per 300 mg of particles and aspirated into 3 cc syringe. The filled 3 cc syringe and a 1 cc empty syringe were attached to a 3-way stopcock. Settling of the particles was prevented by shuttling the suspension back forth between the two syringes.

The stopcock assembly was attached to the placed 5-Fr (0.038" ID) multipurpose catheter. The syringe contents were injected with quick strong injections. The loading and injection procedure was repeated until blood flow ceased in the target areas. Blood flow cessation was confirmed by injecting contrast agent.

The syringe contents contained the following particle masses*:

| | |
|---|---|
| 90-180 um: | 110 mg |
| 180-300 um: | 221 mg |
| 300-500 um: | 233 mg* |
| 500-710 um: | 122 mg* |

*an undetermined amount of each of these size ranges did not get injected because of catheter clogging.

The particles were visible en masse under fluoroscopy during the injections in the absence of added contrast agent. They appeared on the fluoroscopy viewing screen like short bursts of white against a black background, similar to the way contrast agents would appear, although no contrast agent was present in the injection solution. Follow-up injection with contrast agent revealed effective embolization of the vascular beds.

The kidneys were explanted and x-rayed ex vivo (FIGS. 1A and 1B). In FIG. 1A, a large branch of the renal artery, about fourth order, (approximately two to three millimeters in diameter) is visibly packed with the embolotherapy material (arrow). The same artery packed with commercially available polymer spheres would not be visible on x-ray. In FIG. 1B, a small renal artery (arrow) is also visibly packed with 100-300 micron particles.

The figures demonstrate that the inherently radiopaque particles of the preferred embodiments produce a visible cast on x-ray that is essentially homogeneously distributed in the different branches of the renal arteries. Embolization procedures are relatively risky and near-prefect control of particle delivery is necessary. Particles visible on x-ray are more controllable than non-visible particles, because their deployment can be monitored in real time for a more accurate determination of the end point of delivery. The instantaneous feedback on particle distribution also permits calibration of the particle size distribution to permit more accurate delivery. The particles of the preferred embodiments also permit monitoring of the embolized tissue and subsequent polymer resorption by x-ray, replacing the biopsy techniques and indirect evaluation procedures presently employed.

The foregoing demonstrates that the polymers of the preferred embodiments have great promise as inherently radiopaque, non-permanent biocompatible embolotherapy agents. Though less than standard amounts were used, effective embolization was realized with dynamic fluoroscopic visualization and subsequently clear x-ray identification of inherently radiopaque particle masses in the vascular bed. It should be noted, because the contrast agent was injected only pre- and post-embolization, the radio-opacity of the particles can be the result of the inherent character of the polymer.

Example 5

In-Vitro Drug Elution Kinetics

This is determined for the release of drug out of certain polymers, based on physiochemical characteristics and solvent extraction requirements at 37° C. under "sink" conditions, and with agitation to ensure dissolution homogeneity. The therapeutic substance (e.g., drug) in a polymer (see table below) may be coated on to the surface of a polymer film surfaces and it may be embedded or blended with the polymer prior to pressing the film which, emulates a embolotherapy product in these tests.

Film size is adjusted to accommodate drug load and detection limits for quantitation. A typical procedure might include compound extraction or precipitation, followed by quantitation using high performance liquid chromatography (HPLC). An appropriate dissolution media such as 3% Bovine Serum Albumin (BSA) or 35% Tween 20 in a phosphate buffer saline (PBS) is used. Dissolution may be determined from 24 hours out to 28 days. After dissolution, the drug content of films and/or media is analyzed. Dissolution rate is calculated for each drug using a mass balance determination from this HPLC assay. The percent dissolved is calculated by using the quantities measured at each time point for the overall dissolution profile.

TABLE 2

Summary of Testing of Tyrosine-Derived Polycarbonate Coatings

Poly (100% DTE) Carbonate
Poly (90% DTE-co-10% DT)Carbonate[1]
Poly (76% DTE-co-24% DT)Carbonate[2]
Poly (67% DTE-co-33% DT)Carbonate
Poly (95% DTE-co-5% PEG 1 K) Carbonate
Poly (97.5% I$_2$DTE-co-2.5% PEG 2 K) Carbonate
Poly (77.5% I$_2$DTE-co-20% I$_2$DT-2.5% PEG 2 K) Carbonate
Poly (67.5% I$_2$DTE-co-30% I$_2$DT-2.5% PEG 2 K) Carbonate TABLE 2-continued Summary of Testing of Tyrosine-Derived Polycarbonate Coatings Poly (70% I$_2$DTE-co-20% I$_2$DT-10% PEG 2 K) Carbonate
Poly (80% I$_2$DTE-co-20% PEG 2 K) Carbonate

[1]Drug elution was tested in coated films as well as films with the drug embedded.
[2]Drug elution was tested only in films with the drug embedded.

Figure 2:
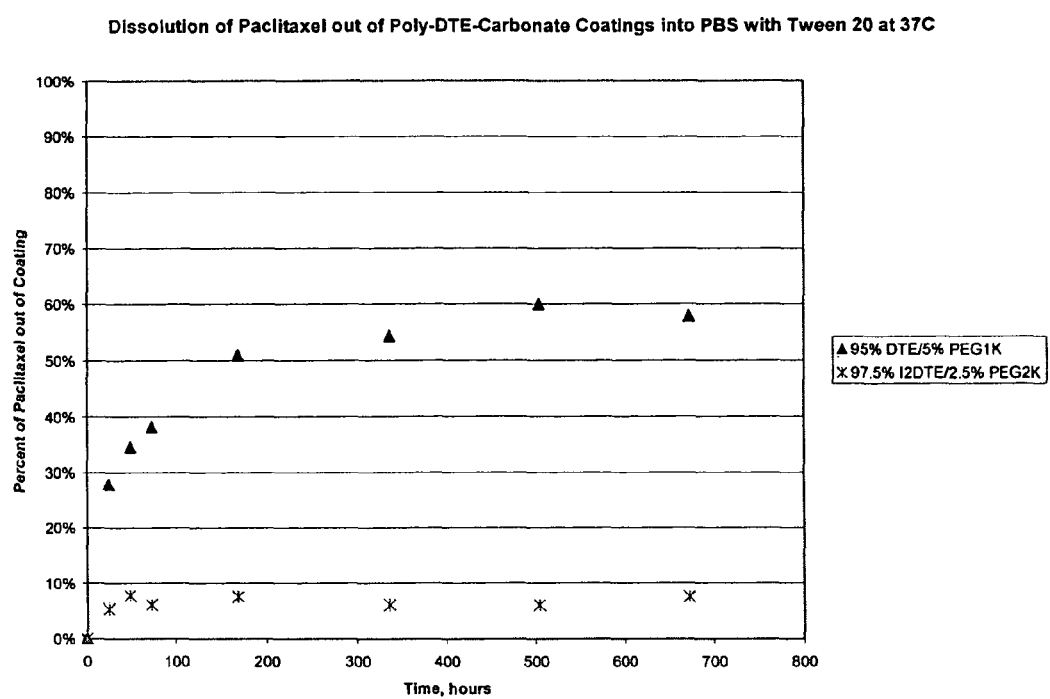
FIG. 2 depicts dissolution of an example chemotherapeutic drug (Paclitaxel) out of poly-DTE-carbonate coating, a biocompatible polymeric embolotherapy coating, according to preferred embodiments into PBS with Tween 20 at 37° C.

Drug elution with the various polymers (TABLE 2) that were coated onto a surface or embedded in the polymer and compressed into a film has demonstrated drug elution. FIG. 2 shows that elution of chemotherapeutic agent out of poly-DTE-carbonates. Other biocompatible bioresorbable polymers may be used for this purpose. In the example of the polycarbonates, drug elution can be tailored by modifying the polymer with iodines on the DAT ring or by adding PEG to the back bone of the polymer.

Example 6

Preparation of Poly(I$_2$DTE-co-2.5 mole % PEG$_{2k}$ Adipate)

The diphenol I$_2$DTE (2.97 g, 4.87 mmol), PEG2000 (0.250 g, 0.125 mmol) and adipic acid (0.731 g, 5.04 mmol) and 0.4 g of DPTS (dimethylamonopyridyl-paratoluene sulfonate, catalyst) were weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Example 7

Polymerization of Poly(60% I$_2$DTE-co-20% I$_2$DT-co-20% PEG$_{2k}$ Adipate)

The diolic components (1.83 g, 3.00 mmol of I$_2$DTE, 0.638 g, 1.00 mmol I$_2$DTtB, and 2.000 g 1.00 mmol of PEG2000), and the diacid (0.731 g, 5 mmol adipic acid) and 0.4 g, of DPTS were weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture, with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Deprotection:

The resulting polymer is dissolved in trifluoroacetic acid (10% w/v) and allowed to stir overnight. The following day, the polymer is precipitated in isopropanol using a blender for mixing. The polymer is then ground twice with fresh isopropanol, filtering with a fritted filter between washes. Then the polymer is dried under nitrogen, followed by drying in a vacuum oven.

Example 8

Preparation of Poly($I_2$DTE-co-2.5 mole % $PEG_{2k}$ Sebacate)

The diphenol $I_2$DTE (2.98 g, 4.89 mmol), PEG2000 (0.250 g, 0.125 mmol) and sebacic acid (1.01 g, 5.00 mmol) and 0.4 g of DPTS are weighed into a 100 ml brown bottle with Teflon-lined cap. To the bottle is also added 40 ml of methylene chloride, and securely capped. The bottle is agitated for 10-15 min and then 2.5 ml (2.02 g, 16 mmol) of diisopropylcarbodiimide is added and continued to agitate for 2 h. An aliquot of the sample is withdrawn and after proper treatment analyzed by GPC. A Mw of about 100,000 is desirable. Once the desired Mw is reached, 200 ml of 2-propanol is added to the reaction mixture, with stirring. The precipitate is collected and dried in a stream of nitrogen. The precipitate is then dissolved in 20 ml of methylene chloride and precipitated with 200 ml of methanol. Then the polymer is dried under nitrogen, followed by drying in a vacuum oven.

Example 9

Preparation of Tri-Iodinated-DTE ($I_2$DITE)

Tri-iodinated monomer ($I_2$DITE) was prepared using procedures similar to those published in the literature by substituting $I_2$DAT in the place of DAT and ITE in the place of TE. In a typical procedure 85.8 g (0.255 mol) of 3-iodotyrosine ethyl ester (ITE), 104 g (0.250 mol) of $I_2$DAT and 3 g (0.025 mol) 1-hydroxybenzotriazole were stirred with 500 ml of tetrahydrofuran in a 1 liter round-bottomed flask. The flask was cooled in an ice-water bath to 10-18° C. and 50 g (0.255 mol) of EDCI was added and stirred for 1 h at 15-22° C. This was followed by stirring of the reaction mixture at ambient temperature for 5 h. The reaction mixture was concentrated to 250 ml and then stirred with 1 L of water and 1 L of ethyl acetate. The lower aqueous layer was separated and discarded using a separatory funnel. The organic layer was sequentially washed with 500 ml each of 0.4 M HCl, 5% sodium bicarbonate solution and 20% sodium chloride solution. After drying over anhydrous sodium sulfate, the organic layer was concentrated to syrup and triturated by stirring with hexane. An off white solid is obtained. The product is characterized by HPLC and $^1$H NMR.

Example 10

Preparation of Tetraiodinated DTE ($I_2DI_2$TE)

DTE (16.4 g, 0.046 mol) was dissolved in 300 ml of 95% ethanol. To the solution with stirring was added 46 g (0.19 mol) of PyICl. The solution was stirred for 2 h when the solid slowly dissolved to give a light yellow solution. This was added over 30 min, with stirring, to 1 liter of water containing 10 g sodium thiosulfate. An off-white solid separated and was isolated by filtration and washed with several portions of deionized water.

The wet cake (ca 150 g) was heated with 1.5 L of ethanol until it dissolved and then allowed to cool to room temperature. The white crystalline solid formed was isolated by filtration and washed with 95% ethanol and dried. 32 g (81%) of the dry product was obtained. The product was characterized by HPLC and $^1$H NMR.

Example 11

Tri-Iodinated Polymer Containing Poly(Ethylene Glycol)

A polymer containing 80% mole percent $I_2$DITE and 20% poly(ethylene glycol) of molecular weight 2000 (poly(80% $I_2$DITE-co-20% PEG2K carbonate)) was prepared as follows. Into a three necked round-bottomed flask, equipped with a mechanical stirrer, a thermometer, a reflux condenser and a rubber septum were added 6.0 g (8.1 mmol) of $I_2$DITE and 4.1 g (2.05 mmol) of PEG2000, and 66 ml of methylene chloride and 3.1 ml (39 mmol) of pyridine. On stirring a clear almost colorless solution was obtained. In a gas tight plastic syringe was placed 6.5 ml of a 20% solution of phosgene in toluene (12.5 mmol), which was then added to the reaction flask over 3 h using a syringe pump. The molecular weight was determined by analyzing an aliquot of the reaction mixture by GPC. A polystyrene equivalent Mw of 200,000 was obtained. The reaction mixture was quenched with 55 ml of tetrahydrofuran and 5 ml of water. The polymer was precipitated by adding the reaction mixture to 1 L of cold 2-propanol in a high speed Waring blender. The resulting gluey polymer was ground with two portions of 0.5 L 2-propanol. The fine granular polymer particles were isolated by filtration and dried in a vacuum oven.

Example 12

Tetra-Iodinated Polymer Containing Poly(Ethylene Glycol)

A polymer containing 80% mole percent $I_2DI_2$TE and 20% poly(ethylene glycol) of molecular weight 2000 (poly(80% $I_2DI_2$TE-co-20% PEG2K carbonate)) was prepared as follows. Into a three necked round-bottomed flask, equipped with a mechanical stirrer, a thermometer, a reflux condenser and a rubber septum were added 1.55 g (1.80 mmol) of $I_2DI_2$TE and 0.9 g (0.45 mmol) of PEG2000, and 20 ml of methylene chloride and 0.68 ml (8.6 mmol) of pyridine. On stirring a clear almost colorless solution was obtained. In a gas tight plastic syringe was placed 1.4 ml of a 20% solution of phosgene in toluene (2.7 mmol), which was then added to the reaction flask over 3 h using a syringe pump. The molecular weight was determined by analyzing an aliquot of the reaction mixture by GPC. A poly-styrene equivalent Mw of 25,000 was obtained. The reaction mixture was quenched with 18 ml of tetrahydrofuran and 2 ml of water. The polymer was precipitated by adding the reaction mixture to 200 ml of cold 2-propanol in a beaker using a magnetic stirrer. The resulting gluey polymer was ground with 200 ml of 2-propanol. The polymer obtained was still gluey probably due to the low molecular weight and high poly(ethylene glycol) content.

Figure 3A:
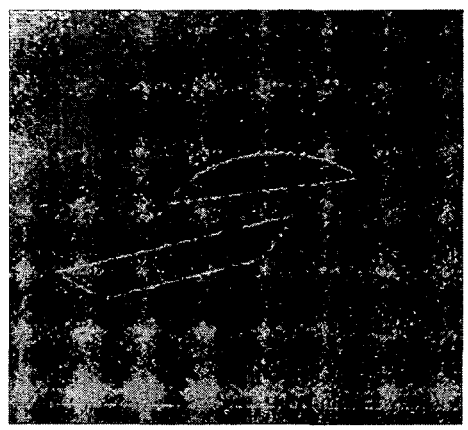
FIGS. 3a-b depicts an X-ray comparison of a radiopaque bioresorbable tri-iodinated tyrosine-derived polycarbonate films showing the radiopacity according to one preferred embodiment of the present invention. The poly(I2DITE-co-20% PEG2K) carbonate films have a photo-density equivalent to human bone.
Figure 3A:
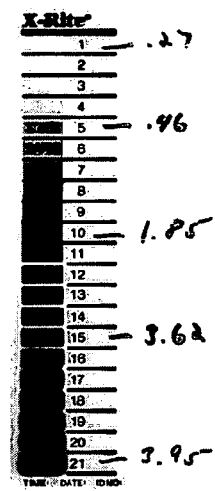
Figure 3B:
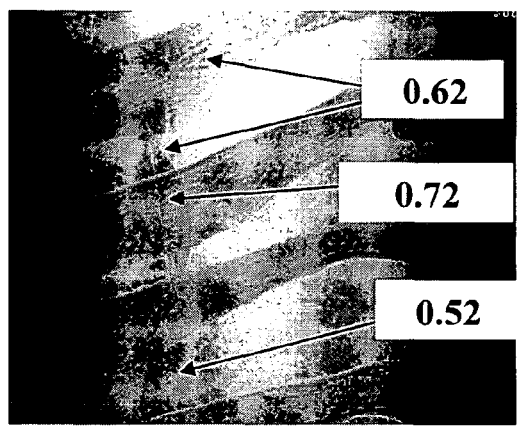
Figure 3B:
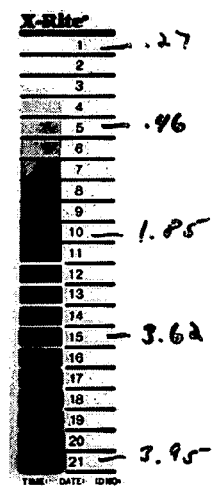

FIG. 3a-b show X-ray comparisons of radiopaque bioresorbable di-iodinated and tri-iodinated tyrosine-derived polycarbonate films. The poly(I2DITE-co-20% PEG2K) carbonate 114 micron films have a photo-density equivalent to human bone. That of poly(80% I2DTE-co-20% PEG2K) carbonate has a lower photo-density.

Example 13

Fibrinogen Adsorption to Polymeric Surfaces

The time course of human fibrinogen adsorption to the test polymer surfaces were measured using a Quartz Crystal Microbalance with Dissipation monitoring (QCM-D, Q-Sense AB, model D300, Goeteborg, Sweden).

QCM-D is a gravimetric technique and useful for measuring in real-time the mass of material in liquid adhering to a surface. An increase in mass bound to the quartz surface causes the crystal's oscillation frequency to decrease. Moreover, this device can measure the change of dissipation induced by the surface-adsorbed mass.

Quartz crystals (Q-Sense, Cat # QSX-301) were spin-coated with polymer solutions (1% polymer in methylene chloride). Commercially available quartz crystals coated with a thin layer of stainless steel (Q-Sense, Cat # QSX-304) were included for comparison. To start a typical experiment, the crystals were inserted into the QCM-D instrument and incubated in phosphate-buffered saline (PBS) at 37° C. After reaching a stable baseline, the fibrinogen solution was injected and the frequency and dissipation shifts induced by adsorbed mass, were recorded in real-time. The fibrinogen solution was incubated until the binding saturation was reached (as indicated by absence of further significant changes in frequency and dissipation values). PBS without fibrinogen was used for all rinsing steps to remove non-bound fibrinogen from the sensor surface after the adsorption process. Human fibrinogen was purchased from Calbiochem (Cat #341576) and diluted in PBS to a final concentration of 3 mg/ml. All experiments were performed in triplicate with a standard deviation of less than 12% (standard error mean).

The quartz crystals could be reused up to 10 times by applying the following cleaning procedure: Quartz crystals were treated with a cleaning solution (80° C., 15 min) consisting of $H_2O_2$ (30%), $NH_4OH$ and ultrapure water in a 1:1:5 ratio. Thereafter, crystals were extensively rinsed with ultrapure water and blow dried with nitrogen. Finally, the crystals were exposed to UV and ozone for 15 min (UVO cleaner, Jelight Company, Irvine, Calif., USA).

TABLE 3 summarizes the comparative evaluation of different stent polymer formulations with respect to fibrinogen adsorption in vitro. Fibrinogen is a key blood protein. The degree of fibrinogen adsorption on an artificial surface in contact with blood is widely regarded as a reliable indicator of the tendency of said surface to be hemocompatible. As a general rule, known to those skilled in the art of biomedical engineering, the lower the level of fibrinogen adsorption onto a material, the higher the hemocompatibility of that material.

TABLE 3

Relative levels of fibrinogen adsorption on test surfaces as measured in vitro by the frequency shift of a quartz microbalance (Q-sense)

| Item | Test material | Fibrinogen adsorption (relative units) |
|---|---|---|
| 1 | Stainless Steel, SS2343 | 83 |
| 2 | PET (Dacron) | 179 |
| 3 | poly(DTE-carbonate) | 158 |
| 4 | poly(I$_2$DTE-carbonate) | 133 |
| 5 | poly(76% DTE-co-24% DT-carbonate) | 125 |
| 6 | poly(I$_2$DTE-co-2.5% PEG2000-carbonate) | 100 |
| 7 | poly(I$_2$DTE-co-3.4% PEG2000-carbonate) | 72 |

In reference to TABLE 3, item 1 (stainless steel) represents a clinically used material, which is known for its low level of thrombogenicity and its good hemocompatibility. Stainless steel serves as a control and has an acceptable level of fibrinogen adsorption. Item 2 in TABLE 3 is Dacron, a known thrombogenic material which has only limited clinical utility in vascular applications. Dacron has the highest level of fibrinogen adsorption of all test materials. Item 3 is poly(DTE carbonate), the base material among the polymers represented by Formula I. Its high level of fibrinogen adsorption indicates that this polymer is not a promising candidate for use in a blood-contacting medical device. Either incorporation of iodine alone (Item 4) or incorporation of DT Units alone (Item 5) tend to reduce the level of fibrinogen adsorption.

The foregoing demonstrates that the simultaneous incorporation of iodine, DT, and PEG results in a major reduction in fibrinogen adsorption—at PEG levels that are still compatible with the need to provide a mechanically strong polymer. Within this general regimen, applicants now provide yet another unexpected observation: Comparison of items 6 and 7 shows that a very small, incremental increase in the amount of PEG within the polymer composition can have a non-obvious and non-predictable effect on protein adsorption. Fibrinogen adsorption to polymer composition 6 is sufficiently low to qualify this composition as a promising candidate material for use in less thrombogenic applications while as little as 0.9 mol % of additional PEG added to polymer composition 7 provided a polymer composition which appears to be superior in terms of its hemocompatibility to the clinically used stainless steel.

Polymer composition 7 in TABLE 3 illustrates another key design principle recognized for the first time by the applicants: When iodine and PEG are incorporated concomitantly into a polymer composition covered by Formula I, a very low molar ratio of PEG is sufficient to reduce dramatically the level of fibrinogen surface adsorption. In combination with the previously described effect of iodine and PEG on the mechanical properties of the polymer composition, applicants have discovered a method to simultaneously optimize both the mechanical and biological properties of polymers. Accordingly, the level of thrombogenicity (i.e., increased and decreased affinity for blood cells and proteins and other molecules related to thrombus formation) can be engineered into the embolotherapy product by varying the relative levels of iodine and percent PEG, DT and DTE.

In addition the embolotherapy products may be delivered or be coated with other biocompatible bioresorbable polymers predetermined to promote biological responses in the embolized body lumen desired for certain clinical effectiveness. The coating may be selected from the broad class of any biocompatible bioresorbable polymer which may include any one or combination of includes use of tyrosine-derived polycarbonates, tyrosine-derived polyarylates, polyesteramides, polyamide carbonates, trimethylene carbonate, polycaprolactone, polydioxane, polyhydroxybutyrate and polyhydroxyvalerate, poly-glycolide, polylactides and stereoisomers and copolymers thereof for any biocompatible bioresorbable polymer for instance glycolide/lactide copolymers. The coating may act to attract and/or inhibit biological responses.

In one example, the bulk of the embolotherapy product, in this example a particle, may be comprised of a high percentage of PEG in the iodinated polycarbonate composition to allow a desired particle compressibility and elasticity for localized delivery through a catheter. Further the particle may comprise a fibrinogen absorbing coating such as chitosan or poly(DTE carbonate) for desired thrombus formation. Such particles may be generated by any methods and techniques known to those skilled in the art for instance standard powder coating methods used in the pharmaceutical industry, by top coating methods used in the medical device industry which may use drug dryers and spray coaters and dip coaters and the like.

Examples of such methods and techniques are disclosed in: Ravina et al., "Arterial Embolization to Treat Uterine Myomata," *Lancet,* 346, 671-672 (Sep. 9, 1995); Hilal et al., "Therapeutic percutaneous embolization for extra-axial vascular lesions of the head, neck, and spine," *J. Neurosurg.* 43(3), 275-287 (1975); Solomon et al., "Chemoembolization of hepatocellular carcinoma with cisplatin, doxorubicin, mitomycin-C, ethiodol, and polyvinyl alcohol: prospective evaluation of response and survival in a U.S. population," *J Vasc Interv Radiol.,* 10(6), 793-8 Jun. 1999); Tseng et al., "Angiographic embolization for epistaxis: a review of 114 cases." *Laryngoscope,* 108(4 Pt 1), 615-9 (April 1998); Kerber et al., "Flow-controlled therapeutic embolization: a physiologic and safe technique," *Am. J. Roentgenol.,* 134(3), 557-61 (March 1980); Latchaw et al., "Polyvinyl Foam Embolization of Vascular and Neoplastic Lesions of the Head, Neck and Spine," *Radiology,* 131, 669-679 (1978); and Tadavarthy, et al., "Polyvinyl Alcohol (Ivalon) A New Embolic Material," *Am. J. Roentgenol.: Radium Therapy and Nuclear Medicine,* 125, 609-616(1975).

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

REFERENCES CITED

1) U.S. Pat. No. 6,475,477 Radio-opaque polymer biomaterials
2) U.S. Pat. No. 6,358,228 Vasoocclusive device including asymmetrical pluralities of fibers
3) U.S. Pat. No. 6,337,198 Porous polymer scaffolds for tissue engineering
4) U.S. Pat. No. 6,319,492 Copolymers of tyrosine-based polyarylates and poly(alkylene oxides)
5) U.S. Pat. No. 6,284,862 Monomers derived from hydroxy acids and polymers prepared therefrom
6) RE37,160 Synthesis of tyrosine derived diphenol monomers
7) U.S. Pat. No. 6,120,491 Biodegradable, anionic polymers derived from the amino acid L-tyrosine
8) U.S. Pat. No. 6,117,157 Helical embolization coil
9) U.S. Pat. No. 6,103,255 Porous polymer scaffolds for tissue engineering
10) U.S. Pat. No. 6,048,521 Copolymers of tyrosine-based polyarylates and poly(alkylene oxides)
11) U.S. Pat. No. 5,877,224 Polymeric drug formulations
12) U.S. Pat. No. 5,851,508 Compositions for use in embolizing blood vessels
13) U.S. Pat. No. 5,670,602 Synthesis of tyrosine-derived diphenol monomers
14) U.S. Pat. No. 5,658,995 Copolymers of tyrosine-based polycarbonate and poly(alkylene oxide)
15) U.S. Pat. No. 5,587,507 Synthesis of tyrosine derived diphenol monomers
16) U.S. Pat. No. 5,317,077 Polyarylates containing derivatives of the natural amino acid 1-tyrosine
17) U.S. Pat. No. 5,216,115 Polyarylate containing derivatives of the natural amino acid L-tyrosine
18) U.S. Pat. No. 5,198,507 Synthesis of amino acid-derived bioerodible polymers
19) U.S. Pat. No. 5,099,060 Synthesis of amino acid-derived bioerodible polymers
20) U.S. Pat. No. 4,819,637 System for artificial vessel embolization and devices for use therewith
21) U.S. Pat. No. 4,441,495 Detachable balloon catheter device and method of use

OTHER PUBLICATIONS

1) Interventional Radiology, Dandlinger et al, ed., Thieme, N.Y., 1990:295-313.
2) "Polyvinyl Alcohol Foam Particle Sizes and Concentrations Injectable through Microcatheters", JVIR 1998; 9:113-115
3) "Polyvinyl Alcohol Particle Size and Suspension Characteristics", American Journal of Neuroradiology June 1995; 16:1335-1343.
4) Ravina et al., Arterial Embolization to Treat Uterine Myomata, Lancet, Sep. 9, 1995; vol. 346, pp. 671-672.
5) "Therapeutic percutaneous embolization for extra-axial vascular lesions of the head, neck, and spine", Hilal et al., J. Neurosurg. 43(3), 275-287 (1975).
6) "Chemoembolization of hepatocellular carcinoma with cisplatin, doxorubicin, mitomycin-C, ethiodol, and polyvinyl alcohol: prospective evaluation of response and survival in a U.S. population." J Vasc Interv Radiol. 1999 June; 10(6):793-8. Solomon B, Soulen M C, Baum R A, Haskal Z J, Shlansky-Goldberg R D, Cope C.
7) "Hydrogel embolic agents. Theory and practice of adding radio-opacity." Link D P, Mourtada F A, Jackson J, Blashka K, Samphilipo M A. Invest Radiol. 1994 August; 29(8): 746-51.
8) "Angiographic embolization for epistaxis: a review of 114 cases." Tseng E Y, Narducci C A, Willing S J, Sillers M J., Laryngoscope. 1998 April; 108(4 Pt 1):615-9.
9) "Supraselective embolization in intractable epistaxis: review of 45 cases." Moreau S, De Rugy M G, Babin E, Courtheoux P, Valdazo A., Laryngoscope. 1998 June; 108 (6):887-8.
10) "Polyvinyl alcohol particle size and suspension characteristics.", Derdeyn C P, Moran C J, Cross D T, Dietrich H H, Dacey R G Jr., AJNR Am J Neuroradiol. 1995 June-July; 16(6): 1335-43.
11) "Polyvinyl alcohol foam particle sizes and concentrations injectable through microcatheters.", Barr J D, Lemley T J, Petrochko C N., J Vasc Interv Radiol. 1998 January-February; 9(1 Pt 1):113-8.
12) "Flow-controlled therapeutic embolization: a physiologic and safe technique.", Kerber C W., AJR Am J Roentgenol. 1980 March; 134(3):557-61.

13) "Polyvinyl alcohol foam: prepackaged emboli for therapeutic embolization.", Kerber C W, Bank W O, Horton J A., AJR Am J Roentgenol. 1978 June; 130(6):1193-4.

14) Interventional Radiology, Dandlinger et al, ed., Thieme, N.Y., 1990:295-313.

15) "Polyvinyl Alcohol Foam Particle Sizes and Concentrations Injectable through Microcatheters", JVIR 1998; 9:113-115.

16) "Polyvinyl Alcohol Particle Size and Suspension Characteristics", American Journal of Neuroradiology June 1995; 16:1335-1343.

17) "Biodegradable microspheres of poly(DL-lactic acid) containing piroxicam as a model drug for controlled release via the parenteral route.", Lalla J K, Sapna K., J Microencapsul. 1993 October-December; 10(4):449-60.

18) "Gelfoam embolization: a simplified technique.", Bank W O, Kerber C W., AJR Am J Roentgenol. 1979 February; 132(2):299-301.

19) R. E. Latchaw, L. H. Gold: "Polyvinyl Foam Embolization of Vascular and Neoplastic Lesions of the Head, Neck and Spine," Radiology, 131 (1979), 669-679.

20) S. M. Tadavarthy, J. H. Moller, K. Amplatz: "Polyvinyl Alcohol (Ivalon) A New Embolic Material," American Journal of Roentgenology: Radium Therapy and Nuclear Medicine, 125 (1975), 609-616.

21) Kerber, C W, "Catheter therapy: fluoroscopic monitoring of deliberate embolic occlusion." Radiology. 1977 November; 125(2):538-40.

22) Horak, et al., "Hydrogels in endo-vascular embolization. IV. Effect of radiopaque spherical particles on the living tissue." Biomaterials 9, 367-371, 1988.

23) Horak, D et al. "Hydrogels in endovascular embolization. III. Radiopaque spherical particles, their preparation and properties." Biomaterials 8, 142-145, 1987.

What is claimed is:

1. An embolotherapy formulation, comprising polymer particles shaped to embolize a body lumen, the polymer particles being suspended in a pharmaceutically acceptable liquid and having an excluded diameter of from about 10 microns to about 3,000 microns, and comprising polymeric units having a structure according to Formula I:

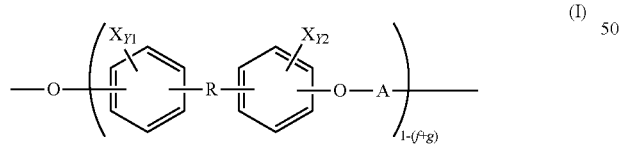
(I)

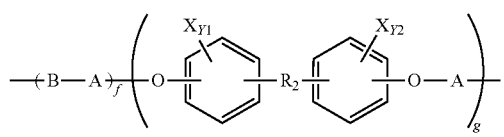

wherein X=I or Br; Y1 and Y2 independently=0, 1, 2, 3 or 4;

wherein f is between 0 and less than 1, g ranges from 0 to 1, inclusive, and f+g is between 0 and 1, inclusive;

wherein R and $R_2$ are independently selected from:

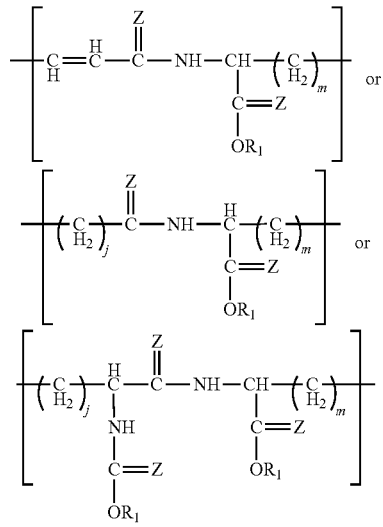

wherein for each $R_2$, each subgroup $R_1$ is an H, and, for each R, each subgroup $R_1$ is independently a long chain aliphatic hydrocarbon;

wherein j and m are independently integers from 1 to 8 inclusive;

wherein Z is independently either O or S;

wherein A is selected from the group consisting of:

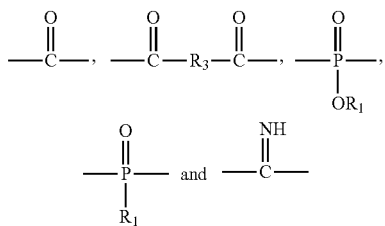

wherein $R_1$ is independently an H or an alkyl group ranging, from 1 to about 18 carbon atoms containing from 0 to 5 heteroatoms selected from O and N; $R_3$ is a saturated or unsaturated, substituted or unsubstituted alkyl, aryl, or alkylaryl group containing up to about 18 carbon atoms and 0 to 8 heteroatoms selected from O and N; and B is an aliphatic linear or branched diol, or a poly(alkylene glycol) unit.

2. A method of embolizing, a body lumen, comprising introducing into the body lumen an effective amount of the embolotherapy formulation of claim 1.

3. The method of claim 2, wherein said introducing is accomplished by injection via either a catheter or syringe.

4. A method of treating varicose and/or spider veins, comprising administering within said varicose and/or spider veins an effective amount of the embolotherapy formulation of claim 1.

5. The method of claim 4, wherein said administering is accomplished by injection via either a catheter or syringe.

6. The embolotherapy formulation of claim 1, wherein Y1 and Y2 are independently 2 or less, and Y1+Y2=1, 2, 3 or 4.

7. The embolotherapy formulation of claim 1, wherein B is a poly(C1-C4 alkylene glycol) unit and said units are present in a weight fraction of less than about 25 wt %.

8. The embolotherapy formulation of claim 7, wherein B is a poly(ethylene glycol) unit.

9. The embolotherapy formulation of claim 1, wherein all X groups are ortho-directed.

10. The embolotherapy formulation of claim 1, wherein g ranges from greater than 0.1 to about 0.35.

11. The embolotherapy formulation of claim 1, wherein said formulation comprises polymer particles selected from the group consisting of spherical particles, geometric-ally non-uniform particles, porous particles, hollow particles, solid particles, and particles having an excluded diameter of from about 1.0 microns to about 3,000 microns, and combinations thereof.

12. The embolotherapy formulation of claim 1, wherein said polymer further comprises an effective amount of at least one therapeutic agent.

13. The embolotherapy formulation of claim 12, wherein said at least one therapeutic agent is selected from the group consisting of a chemotherapeutic agent, a non-steroidal anti-inflammatory, or a steroidal anti-inflammatory.

* * * * *